US008883975B2

(12) United States Patent
Brandt et al.

(10) Patent No.: US 8,883,975 B2
(45) Date of Patent: Nov. 11, 2014

(54) ANTIBODIES AGAINST IL-18R1 AND USES THEREOF

(75) Inventors: Michael Brandt, Iffeldorf (DE); Jens Fischer, Weilheim (DE); Stefan Jenewein, Neustadt/Weinstrasse (DE); Klaus Kaluza, Bad Heilbrunn (DE); Eileen Samy, Jersey City, NJ (US); Stefan Seeber, Penzberg (DE)

(73) Assignee: Hoffmann-La Roche, Inc., Little Falls, NJ (US)

( * ) Notice: Subject to any disclaimer, the term of this patent is extended or adjusted under 35 U.S.C. 154(b) by 495 days.

(21) Appl. No.: 13/218,293

(22) Filed: Aug. 25, 2011

(65) Prior Publication Data

US 2012/0156198 A1 Jun. 21, 2012

(30) Foreign Application Priority Data

Aug. 25, 2010 (EP) .................................. 10174039

(51) Int. Cl.
*C07K 16/00* (2006.01)
(52) U.S. Cl.
USPC .................................... 530/387.1; 424/130.1
(58) Field of Classification Search
None
See application file for complete search history.

(56) References Cited

U.S. PATENT DOCUMENTS

| | | | |
|---|---|---|---|
| 4,676,980 A | 6/1987 | Segal et al. |
| 4,737,456 A | 4/1988 | Weng et al. |
| 4,816,567 A | 3/1989 | Cabilly et al. |
| 5,500,362 A | 3/1996 | Robinson et al. |
| 5,571,894 A | 11/1996 | Wels et al. |
| 5,587,458 A | 12/1996 | King et al. |
| 5,624,821 A | 4/1997 | Winter et al. |
| 5,648,237 A | 7/1997 | Carter |
| 5,648,260 A | 7/1997 | Winter et al. |
| 5,731,168 A | 3/1998 | Carter et al. |
| 5,789,199 A | 8/1998 | Joly et al. |
| 5,821,337 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,600,022 B1 | 7/2003 | Torigoe et al. |
| 6,602,684 B1 | 8/2003 | Umana et al. |
| 6,737,056 B1 | 5/2004 | Presta |
| 7,125,978 B1 | 10/2006 | Vezina et al. |
| 7,141,393 B2 | 11/2006 | Torigoe et al. |
| 7,169,581 B2 | 1/2007 | Sims et al. |
| 7,332,581 B2 | 2/2008 | Presta |
| 7,371,826 B2 | 5/2008 | Presta |
| 7,521,541 B2 | 4/2009 | Eigenbrot et al. |
| 7,615,220 B2 | 11/2009 | Huang et al. |
| 7,704,945 B2 | 4/2010 | Sims et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0123546 A1 | 6/2005 | Umana et al. |
| 2005/0260186 A1 | 11/2005 | Bookbinder et al. |
| 2006/0025576 A1 | 2/2006 | Miller et al. |
| 2006/0104968 A1 | 5/2006 | Bookbinder et al. |
| 2006/0241036 A1 | 10/2006 | Hoshino |
| 2008/0063644 A1 | 3/2008 | Sekiyama |
| 2008/0069820 A1 | 3/2008 | Fuh et al. |

FOREIGN PATENT DOCUMENTS

| | | |
|---|---|---|
| EP | 0 404 097 B1 | 9/1996 |
| EP | 1 047 781 B1 | 7/2004 |
| EP | 1 808 446 | 7/2007 |
| WO | 93/01161 A1 | 1/1993 |
| WO | 93/08829 A1 | 5/1993 |
| WO | 93/16185 A2 | 8/1993 |
| WO | 94/29351 A2 | 12/1994 |
| WO | 94/29351 A3 | 12/1994 |
| WO | 97/30087 A1 | 8/1997 |
| WO | 99/22764 A1 | 5/1999 |
| WO | 99/37772 | 7/1999 |
| WO | 99/51642 | 10/1999 |
| WO | 00/61739 A1 | 10/2000 |
| WO | 01/29246 | 4/2001 |
| WO | 01/85201 A2 | 11/2001 |
| WO | 01/85201 A3 | 11/2001 |
| WO | 02/08272 A2 | 1/2002 |
| WO | 02/08272 A3 | 1/2002 |
| WO | 02/31140 A1 | 4/2002 |
| WO | 03/008452 A2 | 1/2003 |
| WO | 03/008452 A3 | 1/2003 |
| WO | 03/011878 A2 | 2/2003 |
| WO | 03/011878 A3 | 2/2003 |
| WO | 03/012061 A2 | 2/2003 |
| WO | 03/012061 A3 | 2/2003 |
| WO | 03/057821 A2 | 7/2003 |
| WO | 03/057821 A3 | 7/2003 |
| WO | 03/080104 A2 | 10/2003 |

(Continued)

OTHER PUBLICATIONS

Nishida et al. (Hybridoma, vol. 17(6), 1998, p. 577-580).*

(Continued)

*Primary Examiner* — Laura B Goddard
*Assistant Examiner* — Meera Natarajan
(74) *Attorney, Agent, or Firm* — Jennifer L. Davis

(57) ABSTRACT

The invention provides anti-IL-18R1 antibodies and methods of using the same.

22 Claims, 2 Drawing Sheets

(56) References Cited

FOREIGN PATENT DOCUMENTS

| | | |
|---|---|---|
| WO | 03/080104 A3 | 10/2003 |
| WO | 03/084570 A1 | 10/2003 |
| WO | 03/085107 A1 | 10/2003 |
| WO | 03/085119 A1 | 10/2003 |
| WO | 2004/056312 A2 | 7/2004 |
| WO | 2004/056312 A3 | 7/2004 |
| WO | 2005/012352 A1 | 2/2005 |
| WO | 2005/035586 A1 | 4/2005 |
| WO | 2005/035778 A1 | 4/2005 |
| WO | 2005/053742 A1 | 6/2005 |
| WO | 2005/097998 A2 | 10/2005 |
| WO | 2005/097998 A3 | 10/2005 |
| WO | 2005/100402 A1 | 10/2005 |
| WO | 2006/009114 A1 | 1/2006 |
| WO | 2006/029879 A2 | 3/2006 |
| WO | 2006/029879 A3 | 3/2006 |
| WO | 2006/044908 A2 | 4/2006 |
| WO | 2007/096398 A1 | 8/2007 |
| WO | WO 2007/117577 | 10/2007 |
| WO | 2008/027236 A2 | 3/2008 |
| WO | 2008/027236 A3 | 3/2008 |
| WO | 2008/077546 A1 | 7/2008 |
| WO | 98/58964 A1 | 12/2008 |
| WO | 2009/015284 A2 | 1/2009 |
| WO | 2009/015284 A3 | 1/2009 |
| WO | 2009/015284 A8 | 1/2009 |
| WO | 2009/074634 A2 | 6/2009 |
| WO | 2009/074634 A3 | 6/2009 |
| WO | 2009/089004 A1 | 7/2009 |
| WO | 2010/011697 A1 | 1/2010 |

OTHER PUBLICATIONS

Search Report, ROC (TW) Patent Application No. 100130170, Aug. 8, 2013.
Strohl, "Optimization of Fc-mediated effector functions of monoclonal antibodies" Current Opin Biotechnol 20(6):685-691 ( 2009).
Hezareh, M. et al., "Effector function activities of a panel of mutants of a broadly neutralizing abtibody against human immunodeficiency virus type 1." Journal of Virology 75(24):12161-12168 (Dec. 2001).
Hosotani, Y. et al., "Interleukin-18 prevents apoptosis via PI3K/Akt pathway in normal keratinocytes" The Journal of Dermatology 35(8):514-524 (Aug. 8, 2008).
Internet Citation, Other Database, (Retrieved from the internet: URL:http://www.abdserotec.com/uploads/supplement-2003-02.pdf)Other Date 2003.
Internet Citation, Other Database, MAB840, (Retrieved from the internet: URL: http://www.rndsystems.com/pdf/mab840.pdf)Other Date Feb. 18, 2005.
Kang, M. et al., "IL-18 is induced and IL-18 receptor alpha plays a critical role in the pathogenesis of cigarette smoke-induced pulmonary emphysema and inflammation" Journal of Immunology 178(3):1948-1959 (Feb. 1, 2007).
Kunikata, T. et al., "Constitutive and induced IL-18 receptor expression by various peripherl blood cell subsets as deteminted by anti-HIL-18R monoclonal antibody" Cellular Immunology 189:135-143 (Nov. 1, 1998).
Nishida, Y. et al., "Cloning and expression of a single-chain FV fragment specific for the human interleukin 18 receptor" Hydridoma 17(6):577-580 (Dec. 1, 1998).
Vermont-Desroches, C. et al., "Monoclonal antibodies specific fot the IL-18 receptor" Cellular Immunology 236(1-2):101-104 (Jul. 1, 2005).
Zhang, B. et al., "Expression of IL-18 and its receptor in human leukemia cells" Leukemia Research 27(9):813-822 (Jan. 1, 2003).
Angal et al., "A single amino acid substitution abolishes the heterogeneity of chimeric mouse/human (IgG4) antibody" Molec Immunol 30(1):105-108 (Jan. 1, 1993).
Brennan et al., "Preparation of bispecific antibodies by chemical recombination of monoclonal immunoglobulin $G_1$ fragments" Science 229:81-83 ( 1985).
Brueggemann et al., "Comparison of the effector functions of human immunoglobulins using a matched set of chimeric antibodies" J. Exp. Med. 166:1351-1361 ( 1987).
Charlton, "Expression and Isolation of Recombinant Antibody Fragments in *E. coli*" Method Molec Biol 248:245-254 ( 2003).
Chen et al., "Selection and analysis of an optimized anti-VEGF antibody: Crystal structure of an affinity-matured Fab in complex with antigen" J Mol Biol 293:865-881 ( 1999).
Clackson et al., "Making antibody fragments using phage display libraries" Nature 352:624-628 (Aug. 15, 1991).
Clynes et al., "Fc Receptors Are Required in Passive and Active Immunity to Melanoma" P Natl Acad Sci USA 95(2):652-656 (Jan. 1998).
Cragg et al., "Antibody specificity controls in vivo effector mechanisms of anti-CD20 reagents" Blood 103(7):2738-2743 ( 2004).
Cragg et al., "Complement-mediated lysis by anti-CD20 mAb correlates with segregation into lipid rafts" Blood 101(3):1045-1052 ( 2003).
Duncan and Winter, "The binding site for C1q on IgG" Nature 322:738-740 ( 1988).
Flatman et al., "Process analytics for purification of monoclonal antibodies" J Chromatogr 848:79-87 ( 2007).
Freeman et al., "Cytotoxic potential of lunch $CD8^+$ T Cells Increases with chronic obstructive pulmonary disease severity and with in vitro stimulation by IL-18 or IL-15" J Immunol 184:6504-6513 ( 2010).
Gazzano-Santoro et al., "A non-radioactive complement-dependent cytotoxicity assay for anti-CD20 monoclonal antibody" J Immunol Methods 202(2):163-171 (Mar. 28, 1997).
Gerngros, "Advances in the production of human therapeutics in yeasts and filamentous fungi" Nature Biotechnology 22(11):1409-1414 (Nov. 2004).
Graham et al., "Characteristics of a human cell line transformed by DNA from human adenovirus type 5" J Gen Virol 36(1):59-72 (Jul. 1977).
Gruber et al., "Efficient Tumor Cell Lysics Mediated by a Bispecific Single Chain Antibody Expressed in *Escherichia coli*" J Immunol 152:5368-5374 ( 1994).
Grumelli et al., "An immune bases for lung parenchymal destruction in chronic obstructive pulmonary disease and emphysema" PLoS Med 1(1 Suppl e8):075-083 (Oct. 2004).
Guyer et al., "Immunoglobulin Binding by Mouse Intestinal Epithelial Cell Receptors" J Immunol 117(2):587-593 ( 1976).
Hellstrom et al., "Antitumor effects of L6, and IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Holliger et al., "'Diabodies': small bivalent and bispecific antibody fragments" P Natl Acad Sci USA 90:6444-6448 (Jul. 1993).
Hoshino et al., "Pulmonary inflammation and emphysema, Role of the cytokines IL-18 and IL-13" Am J Respir Crit Care Med 176:49-62 ( 2007).
Hudson et al., "Engineered antibodies" Nature Medicine 9(1):129-134 (Jan. 2003).
Idusogie et al., "Mapping of the C1q binding site of Rituxan, a chimeric antibody with a human IgG1 Fc" J Immunol 164:4178-4184 ( 2000).
International Search Report and Written Opinion for International Patent Application No. PCT/EP2011/064487.
Kabat et al. Sequences of Proteins of Immunological Interest 5th edition,NIH,:2 pages ( 1991).
Kabat et al. U.S. Dept. of Health and Human Services (Publication No. 91-3242), Fifth edition, ( 1991).
Kam et al., "Carbon nanotubes as mulifunctional biological transporters and near-infrared agents for selective cancer cell destruction" P Natl Acad Sci USA 102(33):11600-11605 (Aug. 2005).
Kanda et al., "Comparison of cell lines for stable production of fucose-negative antibodies with enhanced ADCC" Biotechnol Bioeng 94(4):680-688 (Jul. 5, 2006).
Kang et al., "Cigarette smoke selectively enhances viral PAMP—and virus-induced pulmonary innate immune and remodeling responses in mice" J Clin Invest 118(8):2771-2784 (Aug. 2008).

(56) References Cited

OTHER PUBLICATIONS

Kearns and Hoffmann, "Integrating computational and biochemical studies to explore mechanisms in NF κB signaling" J Biol Chem 284(9):5439-5443 (Feb. 27, 2009).

Kim et al., "Localization of the site of the murine IgG1 molecule that is involved in binding to the murine intestinal Fc receptor" Eur J Immunol 24(10):2429-2434 (Oct. 1994).

Kindt et al. Kuby Immunology 6th ed edition, N.Y.:W.H. Freeman and Co,:p. 91 ( 2007).

Kostelny et al., "Formation of a bispecific antibody by the use of leucine zippers" J Immunol 148(5):1547-1553 (Mar. 1, 1992).

Li et al., "Optimization of humanized IgGs in glycoengineered Pichia pastoris" Nat Biotechnol 24(2):210-215 (Feb. 2006).

Ma et al., "Role of CCR5 in IFN-γ-induced and cigarette smoke-induced emphysema" J Clin Invest 115(12):3460-3472 (Dec. 2005).

Mather, "Establishment and Characterization of Two Distinct Mouse Testicular Epithelial Cell Lines" Biol Reprod 23:243-252 ( 1980).

Milstein and Cuello, "Hybrid hybridomas and their use in immunohistochemistry" Nature 305:537-540 (Oct. 6, 1983).

Nakanishi et al., "Interleukin-18 regulates both TH1 and TH2 responses" Annu Rev Immunol 19:423-474 ( 2001).

Okazaki et al., "Fucose depletion from human IgG1 oligosaccharide enhances binding enthalpy and association rate between IgG1 and FycγRIIIa" J Molec Biol 336:1239-1249 ( 2004).

Parnet et al., "IL-1Rrp is a novel receptor-like molecule similar to the type I interleukin-1 receptor and its homologues T1/ST2 and IL-1R AcP" J Biol Chem 271(8):3967-3970 (Feb. 23, 1996).

Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).

Pluckthun The Pharmacology of Monoclonal Antibodies: Handbook of Pharmacology "Antibodies from *Escherichia coli*" (Chapter 11), Rosenberg and Moore, eds., Berlin:Springer-Verlag, vol. 113:269-315 ( 1994).

Portolano et al., "Lack of Promiscuity in Autoantigen-Specific H and L Chain Combinations as Revealed by Human H and L Chain 'Roulette'" J Immunol 150(3):880-887 (Feb. 1993).

Ravech and Kinet, "Fc Receptors" Ann Rev Immunol 9:457-492 ( 1991).

Remington's Pharmaceutical Sciences, Oslo et al., eds., 16th edition, Mack Publishing Co. (1980).

Ripka et al., "Two chinese hamster ovary glycosylation mutants affected in the conversion of GDP-mannose to GDP-fucose" Arch Biochem Biophys 249(2):533-545 (Sep. 1986).

Shields et al., "High Resolution Mapping of the Binding Site on Human IgG1 for FcγRI, FcγRII, FcγRIII, and FcRn and Design of IgG1 Variants with Improved Binding to the FcγR" J Biol Chem 276(9):6591-6604 (Mar. 2, 2001).

Shirai et al., "Correlation between peripheral blood T-cell profiles and clinical and inflammatory parameters in stable COPD" Allergol Int 59:75-82 ( 2010).

Sutherland et al., "Management of chronic obstructive pulmonary disease" New Engl J Med 350(26):2689-2697 (Jun. 24, 2004).

Tominaga et al., "IL-12 synergizes with IL-18 or IL-1B for IFN-y production from human cells" Int Immunol 12(2):151-160 ( 2000).

Torigoe et al., "Purification and characterization of the human interleukin-18 receptor" J Biol Chem 272(41):25737-25742 (Oct. 10, 1997).

Traunecker et al., "Bispecific single chain molecules (Janusins) target cytotoxic lymphocytes on HIV infected cells" EMBO J 10(12):3655-3659( 1991).

Tutt et al., "Trispecific F(ab')₃ derivatives that use cooperative signaling via the TCR/CD3 complex and CD2 to activate and redirect resting cytotoxic T cells" J Immunol 147(1):60-69 (Jul. 1991).

Urlaub et al., "Isolation of chinese hamster cell mutants deficient in dihydrofolate reductase activity" P Natl Acad Sci USA 77(7):4216-4220 (Jul. 1980).

Wang et al., "Interferon γ induction of pulmonary emphysema in the adult murine lung" J Exp Med 192(11):1587-1599 (Dec. 4, 2000).

Wright and Morrison, "Effect of Glycosylation on Antibody Function: Implications for Genetic Engineering" Trends Biotechnol 15:26-32 ( 1997).

Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-522 (Sep. 5, 2004).

Yazaki et al., "Expression of Recombinant Antibodies in Mammalian Cell Lines" Methods Molec Biol 248:255-268 ( 2004).

Zhu et al., "Peripheral T cell functions correlate with the severity of chronic obstructive pulmonary disease" J Immunol 182:3270-3277 ( 2009).

\* cited by examiner

US 8,883,975 B2

ANTIBODIES AGAINST IL-18R1 AND USES THEREOF

RELATED APPLICATIONS

This application claims of priority under 35 USC §119(a) to European patent application number 10174039.7, filed Aug. 25, 2010, the contents of which are incorporated herein by reference.

FIELD OF THE INVENTION

The present invention relates to antibodies against human IL-18R1 (IL-18R1 antibody or IL-18Rα antibody). The antibodies described herein do not bind complement factor C1q. Also provided for herein are methods for their production, pharmaceutical compositions containing said antibodies, and uses thereof.

BACKGROUND OF THE INVENTION

IL-18 is a member of the IL-1 cytokine superfamily. It is an important regulator of innate and adaptive immunity, it synergizes with IL-12 to induce Th1/Tc1 lineage differentiation, induces T and NK cell maturation, stimulates IFNγ, TNF-α and GM-CSF production, regulates macrophage and neutrophil accumulation, function and cellular apoptosis, and contributes to Th2 responses by stimulating IgE production and Th2 differentiation in the presence of IL-4 or IL-2. IL-18 receptor (IL-18R1) consists of a ligand binding (IL-18Rα) and signaling transducing subunits (IL-18Rβ) (reviewed in Nakanishi, K. et al., Ann. Rev. Immunol. 19 (2001) 423-474).

IL-18 appears to modulate inflammation at multiple checkpoints and considered a potential therapeutic target. Previous studies have demonstrated that IFNα and CD8 T-cells plays an important role(s) in the pathogenesis of pulmonary emphysema (Grumelli, S. et al., PLoS Medicine 1 (2004) 75-83; Ma et al., J. Clin. Invest. 115 (2005); 3460-3472; Wang, Z. et al., J. Exp. Med. 192 (2000) 1587-1599; Sutherland and Cherniack, N. Engl. J. Med. 350 (2004) 2689-2697. IL-18 plays an important role in Th1/Tc1 lineage differentiation and cytokine production. Hoshino, T. et al., Am. J. Respir. Crit. Care Med. 176 (2007) 49-62. In a murine model, cigarette smoke (CS) induces and activates IL-18 in mice, IL-18R1α plays a critical role in the pathogenesis and CS-induced inflammation and alveolar destruction (Kang, M. J., et al., J. Immunol. 178 (2007) 1948-1959; Kang, M. J., J. Clin. Invest. 118 (2008) 2771-2784).

Human IL-18R1 (Interleukin-18 receptor 1, IL-18Rα, CD218 antigen-like family member A, CD218a, UniProtKB/Swiss-Prot Q13478; SEQ ID NO:72) is a receptor for interleukin 18 (IL-18) and a Single-pass type I membrane protein. Binding to the agonist leads to the activation of NF-kappa-B. IL-18R1 is expressed in lung, leukocytes, spleen, liver, thymus, prostate, small intestine, colon, placenta, and heart, and is absent from brain, skeletal muscle, pancreas, and kidney. High level of expression are found in Hodgkin disease cell lines. IL-18R1 is mentioned in Parnet, P. et al., J. Biol. Chem. 271 (1996) 3967-3970; Torigoe, K. et al., J. Biol. Chem. 272 (1997) 25737-25742).

IL-18R1 and antibody against IL-18R1 are mentioned U.S. Pat. No. 7,704,945, U.S. Pat. No. 7,615,220, U.S. Pat. No. 7,169,581, U.S. Pat. No. 7,141,393, U.S. Pat. No. 6,600,022, EP1047781, WO2010011697, WO2009015284, WO2009015284, WO2009074634, WO2009015284, WO2007117577, WO2008027236, WO2007117577, WO2007096398, WO2005097998A3, WO2006009114, WO2005097998, WO2005012352, WO2003080104, WO2003057821, WO2003008452A3, WO2003012061, WO2001085201, WO2002008272, WO1999037772.

The object of the invention is to provide antibodies against IL-18R1 which are useful as a therapeutic agent for treatment of inflammatory diseases, like TH1 mediated diseases especially COPD, autoimmune diseases, rheumatoid arthritis, lupus, and psoriasis diseases.

SUMMARY OF THE INVENTION

The invention relates to an isolated antibody that binds to human IL-18R1 and being characterized in binding to the same human IL-18R1 epitope to which the monoclonal antibody 1G12 binds. Mab 1G12 comprises as amino acid sequence of the variable heavy chain region SEQ ID NO:1 and as amino acid sequence of the variable light chain region SEQ ID NO:5. The antibodies described herein bind to human IL-18R1 with a binding affinity of $10^{-8}$ M or less.

In one aspect, the invention relates to an isolated antibody that binds to human IL-18R1 and being characterized in comprising as heavy chain variable region CDRs a CDRH1 region of SEQ ID NO:2 or SEQ ID NO:10, a CDRH2 region of SEQ ID NO:3 and a CDRH3 region of SEQ ID NO:4, and as light chain variable region CDRs a CDRL1 region of SEQ ID NO:6, a CDRL2 region of SEQ ID NO:7 and a CDRL3 region of SEQ ID NO:8. Therefore, only the CDRH1 region of antibodies 1G12 and 2D11 are different and the other CDR regions are identical (cf. III. Description of the sequence listing).

One embodiment of the invention is an isolated antibody binding to human IL-18R1 and being characterized in comprising as heavy chain variable region CDRs a CDRH1 region of SEQ ID NO:2 or SEQ ID NO:10, a CDRH2 region of SEQ ID NO:3 and a CDRH3 region of SEQ ID NO:4, and as light chain variable region CDRs a CDRL1 region of SEQ ID NO:6, a CDRL2 region of SEQ ID NO:7 and a CDRL3 region of SEQ ID NO:8 or a humanized version thereof. In one embodiment the antibody according to the invention is characterized in that the heavy chain variable domain comprises as CDRs a) a CDRH1 region of SEQ ID NO:2, a CDRH2 region of SEQ ID NO:3 and a CDRH3 region of SEQ ID NO:4, or
b) a CDRH1 region of SEQ ID NO:10, a CDRH2 region of SEQ ID NO:3 and a CDRH3 region of SEQ ID NO:4;
or a humanized version thereof of either a or b.

In another embodiment the antibody according to the invention is characterized in that the light chain variable domain comprises as CDRs a CDRL1 region of SEQ ID NO:6, a CDRL2 region of SEQ ID NO:7 and a CDRL3 region of SEQ ID NO:8; or a humanized version thereof.

In another embodiment the antibody according to the invention is characterized in that the heavy chain variable domain and the light chain variable domain comprises as CDRs a) a CDRH1 region of SEQ ID NO:2, a CDRH2 region of SEQ ID NO:3 and a CDRH3 region of SEQ ID NO:4, and a CDRL1 region of SEQ ID NO:6, a CDRL2 region of SEQ ID NO:7 and a CDRL3 region of SEQ ID NO:8, or
b) a CDRH1 region of SEQ ID NO:10, a CDRH2 region of SEQ ID NO:3 and a CDRH3 region of SEQ ID NO:4, and a CDRL1 region of SEQ ID NO:6, a CDRL2 region of SEQ ID NO:7 and a CDRL3 region of SEQ ID NO:8;
or a humanized version thereof of either a or b.

The invention relates to an antibody binding to human IL-18R1 and being characterized in comprising as heavy chain variable region SEQ ID NO:1 and as variable light chain region SEQ ID NO:5 or in comprising as heavy chain variable region SEQ ID NO:9 and as variable light chain region SEQ ID NO:11;
or a humanized version thereof.

In one embodiment the humanized antibody according to the invention is characterized in comprising
- a) as heavy chain variable region CDRs a CDRH1 region of SEQ ID NO:30, a CDRH2 region of SEQ ID NO:31 and a CDRH3 region of SEQ ID NO:32, and as light chain variable region CDRs a CDRL1 region of SEQ ID NO:34, a CDRL2 region of SEQ ID NO:35 and a CDRL3 region of SEQ ID NO:36;
- b) as heavy chain variable region CDRs a CDRH1 region of SEQ ID NO:38, a CDRH2 region of SEQ ID NO:39 and a CDRH3 region of SEQ ID NO:40, and as light chain variable region CDRs a CDRL1 region of SEQ ID NO:42, a CDRL2 region of SEQ ID NO:43 and a CDRL3 region of SEQ ID NO:44;
- c) as heavy chain variable region CDRs a CDRH1 region of SEQ ID NO:46, a CDRH2 region of SEQ ID NO:47 and a CDRH3 region of SEQ ID NO:48, and as light chain variable region CDRs a CDRL1 region of SEQ ID NO:50, a CDRL2 region of SEQ ID NO:51 and a CDRL3 region of SEQ ID NO:52;
- d) as heavy chain variable region CDRs a CDRH1 region of SEQ ID NO:54, a CDRH2 region of SEQ ID NO:55 and a CDRH3 region of SEQ ID NO:56, and as light chain variable region CDRs a CDRL1 region of SEQ ID NO:58, a CDRL2 region of SEQ ID NO:59 and a CDRL3 region of SEQ ID NO:60; or
- e) as heavy chain variable region CDRs a CDRH1 region of SEQ ID NO:62, a CDRH2 region of SEQ ID NO:63 and a CDRH3 region of SEQ ID NO:64, and as light chain variable region CDRs a CDRL1 region of SEQ ID NO:66, a CDRL2 region of SEQ ID NO:67 and a CDRL3 region of SEQ ID NO:68.

In one embodiment the humanized antibody according to the invention is characterized in comprising
- a) as heavy chain variable region SEQ ID NO:29 and as variable light chain region SEQ ID NO:33;
- b) as heavy chain variable region SEQ ID NO:37 and as variable light chain region SEQ ID NO:41;
- c) as heavy chain variable region SEQ ID NO:45 and as variable light chain region SEQ ID NO:49;
- d) as heavy chain variable region SEQ ID NO:53 and as variable light chain region SEQ ID NO:57; or
- e) as heavy chain variable region SEQ ID NO:61 and as variable light chain region SEQ ID NO:65.

In one aspect the anti-IL-18R1 antibody comprises complementarity-determining regions (CDRs) sequences selected from:
- (a) a CDR-L1 sequence comprising amino acids XASKSVSTSGDSYMH (SEQ ID NO:69), where X is either R or Q;
- (b) a CDR-L2 sequence comprising amino acids LASNLES (SEQ ID NO:7);
- (c) a CDR-L3 sequence comprising amino acids QQSRELPLS (SEQ ID NO:8);
- (d) a CDR-H1 sequence comprising amino acids XYTFT (SEQ ID NO:70), where X is either D or G;
- (e) a CDR-H2 sequence comprising amino acids TIDPSDSYTYYX$_1$QKX$_2$X$_3$G (SEQ ID NO: 71), wherein X$_1$ is N or A, X$_2$ is F or A, and X$_3$ is K or Q; and
- (f) a CDR-H3 sequence comprising amino acids SGDYDADRYFDV (SEQ ID NO:4).

In one embodiment the antibody is humanized.

The invention relates to an antibody that binds to human IL-18R1 and being characterized in binding to the same IL-18R1 epitope to which monoclonal antibody 1G12 binds. The antibody binds therefore to domain 2 of IL-18R1. An exemplary antibody is antibody 2D11.

The antibody in one embodiment is a monoclonal antibody. In another embodiment it is a chimeric antibody comprising a human constant chain. In yet another embodiment the antibody is a humanized antibody. Especially preferred is a humanized antibody.

In one embodiment, the antibody comprises an Fc part of human origin or derived therefrom.

In one aspect, the light chain variable domain of the antibody according to the invention are preferably of human lambda isotype. A preferred embodiment of the invention is a chimeric or humanized variant of antibody 1G12 or of antibody 2D11. Preferably the antibody according to the invention is characterized by the above mentioned amino acid sequences or amino acid sequence fragments and properties.

In one aspect, the antibody according to the invention is of human IgG isotype. In one embodiment, the isotype is either IgG1 or IgG4. In an embodiment, the antibody of IgG1 isotype modified in the hinge region at about amino acid position 216-240, preferably at about amino acid position 220-240, between CH1 and CH2 and/or in the second inter-domain region at about amino acid position 327-331 between CH2 and CH3. In one embodiment, the antibody comprises a mutation at a position equivalent to L234 and/or L235 of human IgG1. In a further embodiment, the antibody is a human IgG1 isotype, comprising mutation L234A, which is alanine instead of leucine at amino acid position 234, and mutation L235A, which is alanine instead of leucine at amino acid position 235. The amino acid positions might vary for different allotypes within about one or two numbers, so that leucine at amino acid position 234 could be located e.g. at position 235 in such an allotype. "leucine at amino acid position 234" means therefore leucine located at amino acid position 234 or on or two positions up or down.

In one embodiment, the antibody is of human IgG4 isotype with or without mutation S228P.

In one aspect, the antibody is characterized by an affinity of $10^{-8}$ M ($K_D$) or less, preferably of about $10^{-8}$ to $10^{-13}$ M, preferably of about $10^{-9}$ to $10^{-13}$ M in binding to human IL-18R1. In one embodiment, the antibody binds also (cross reacts) to cynomolgus IL-18R1.

In one aspect, there is provided methods for the recombinant production of antibodies as provided for herein. In one embodiment, the method for the production of a recombinant antibody comprises expressing a nucleic acid encoding an antibody that binds to IL-18R1 in a CHO host cell and recovering said antibody from said cell.

In another aspect, there is provided a nucleic acid encoding an antibody as described herein.

In a further aspect, there is provided the use of an antibody according to the invention for the treatment of Chronic Obstructive Pulmonary Disease (COPD), inflammatory, autoimmune, rheumatoid arthritis, lupus, psoriasis or bone diseases. In one embodiment, there is provided the use of an antibody according to the invention for the manufacture of a medicament for the treatment of diseases, preferably of inflammatory, autoimmune, lupus, psoriasis or bone diseases. In a further embodiment, there is provided a method for the manufacture of a medicament for the treatment of diseases, preferably of Chronic Obstructive Pulmonary Disease (COPD), inflammatory, autoimmune, rheumatoid arthritis, lupus, psoriasis or bone diseases, characterized in comprising an antibody according to the invention. The antibodies according to the invention are characterized by the above mentioned properties.

In a yet further aspect, there is provided methods for treating Chronic Obstructive Pulmonary Disease (COPD), inflammatory, autoimmune, rheumatoid arthritis, lupus, psoriasis or bone diseases, comprising administering to a patient diagnosed as having such disease (and therefore being in need of such a therapy) an antibody against IL-18R1 according to the invention. The antibody may be administered alone, in a pharmaceutical composition, or alternatively in combination with other medicaments for treating Chronic Obstructive Pulmonary Disease (COPD), inflammatory, autoimmune, rheumatoid arthritis, lupus, psoriasis or bone diseases. The antibody is administered in a pharmaceutically effective amount.

In a yet further aspect, there is provided the use of an antibody according to the invention for the treatment of Chronic Obstructive Pulmonary Disease (COPD), inflammatory, autoimmune, rheumatoid arthritis, lupus, psoriasis or bone diseases, and for the manufacture of a pharmaceutical composition according to the invention. In addition, the invention comprises a method for the manufacture of a pharmaceutical composition according to the invention.

In another aspect, there is provided an antibody according to the invention for the treatment of Chronic Obstructive Pulmonary Disease (COPD), inflammatory, autoimmune, rheumatoid arthritis, lupus, psoriasis or bone diseases.

In one aspect, there is provided a pharmaceutical composition containing an antibody according to the invention, optionally together with a buffer and/or an adjuvant useful for the formulation of antibodies for pharmaceutical purposes.

In one aspect, there is provided pharmaceutical compositions comprising such antibodies in a pharmaceutically acceptable carrier. In one embodiment, the pharmaceutical composition may be included in an article of manufacture or kit. The invention further provides the use of an antibody according to the invention for the manufacture of a pharmaceutical composition for the treatment of cancer or Chronic Obstructive Pulmonary Disease (COPD), inflammatory, autoimmune, rheumatoid arthritis, lupus, psoriasis or bone diseases. The antibody is used in a pharmaceutically effective amount.

In a further aspect, the use of an antibody according to the invention for the manufacture of a pharmaceutical composition for the treatment of Chronic Obstructive Pulmonary Disease (COPD), inflammatory, autoimmune, rheumatoid arthritis, lupus, psoriasis or bone diseases is provided. The antibody is used in a pharmaceutically effective amount.

The antibodies according to the invention have new and inventive properties causing a benefit for a patient suffering from a disease associated with IL-18 receptor mediated signaling and NFkappaB pathway activation.

The antibodies according to the invention have new and inventive properties and bind to IL-18R1 and inhibit binding of IL-18 to IL-18R1. As consequence the formation of the complex between IL-18R1 and IL-18RAP is inhibited and signaling caused by the IL-18 receptor complex is inhibited. This inhibits NFkappaB pathway activation.

DETAILED DESCRIPTION OF EMBODIMENTS OF THE INVENTION

I. Definitions

Figure 1:
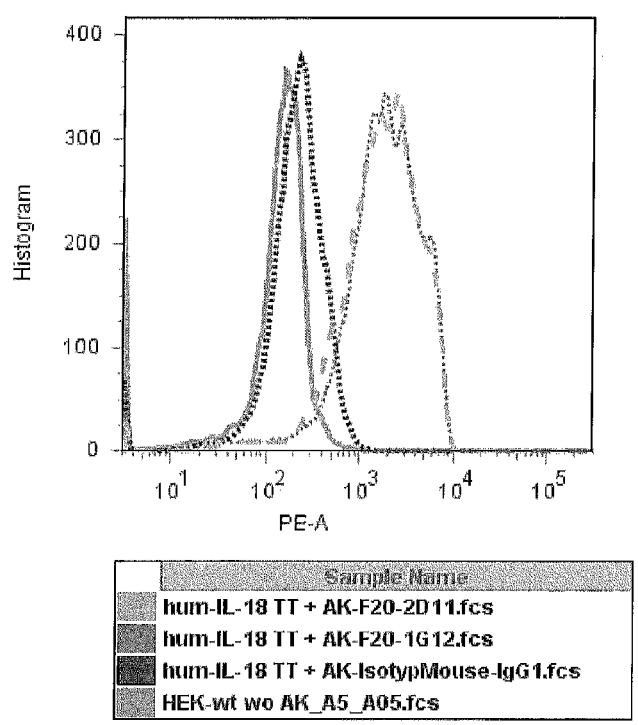
FIG. 1: FACS against human IL-18Rα/IL-18R13 transfected HEK293 cells.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The terms "anti-IL-18R1 antibody" and "an antibody that binds to IL-18R1" refer to an antibody that is capable of binding human IL-18R1 with sufficient affinity such that the antibody is useful as a diagnostic and/or therapeutic agent in targeting IL-18R1. In one embodiment, the extent of binding of an anti-IL-18R1 antibody to an unrelated, non-IL-18R1 protein is less than about 10% of the binding of the antibody to IL-18R1 as measured, by Surface Plasmon Resonance. In certain embodiments, an antibody that binds to IL-18R1 has a dissociation constant (Kd) of $10^{-8}$M or less, e.g. from $10^{-8}$M to $10^{-13}$M, e.g., from $10^{-9}$ M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "cancer" as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The antibody according to the invention is preferably characterized by being of human subclass IgG1 with mutations PVA236, L234A/L235A and/or GLPSS331 (GLPSS331 means that in the 331 region ALPAP of IgG1 or GLPAP of IgG2 is changed to GLPSS) or of subclass IgG4. In a further preferred embodiment of the invention, the antibody is characterized by being of any IgG class, preferably being IgG1 or IgG4, containing at least one mutation in E233, L234, L235, G236, D270, N297, E318, K320, K322, A327, A330, P331 and/or P329 (numbering according to EU index). Especially preferred are the IgG1 mutations PVA236 (PVA236 means that the amino acid sequence ELLG (given in one letter amino acid code) from amino acid position 233 to 236 of IgG1 or EFLG of IgG4 is replaced by PVA), L234A/L235A and/or GLPSS331 as well as the IgG4 mutation L235E. It is further preferred that the antibody of IgG4 subclass contains the mutation S228P or the mutation S228P and L235E (Angal, S., et al., Mol. Immunol. 30 (1993) 105-108). The antibody according to the invention therefore is preferably an antibody of human subclass IgG1, containing one or more mutation(s) from PVA236, GLPSS331 and/or L234A/L235A (numbering according to EU index).

"Disease" refers to an IL-18R1 mediated disease. These IL-18R1 diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, spondyloarthopathy, atheromatous disease1 arteriosclerosis, atopic allergy, autoimmune bullous disease, pemphigus vulgaris, pemphigus foliaceus, pemphigoid, linear IgA disease, autoimmune haemolytic anemia, Coombs positive haemolytic anemia, acquired pernicious anemia, juvenile pernicious anemia, myalgic encephalitis/Royal Free Disease. chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency, common variable hypogammaglobulinemia, dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis, classical autoimmune or lupoid hepatitis, type-2 autoimmune hepatitis, anti-LKM antibody hepatitis, autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropenia, renal disease NOS, glomerulonephritides, microscopic vasulitis of the kidneys, Lyme disease, discoid lupus erythematosus, male infertility idiopathic or NOS, sperm autoimmunity, all subtypes of multiple sclerosis, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopenia, idiopathic thrombocytopenia, autoimmune thyroid disease, hyperthyroidism, goitrous autoimmune hypothyroidism or Hashimoto's disease, atrophic autoimmune hypothyroidism, primary myxoedema, phacogenic uveitis, primary vasculitis, vitiligo, acute liver disease, chronic liver diseases, allergy and asthma, mental disorders, depression, schizophrenia, Th2 Type and Th1 Type mediated diseases, Chronic Obstructive Pulmonary Disease (COPD), inflammatory, autoimmune, lupus (e.g., Systemic Lupus Erythromatosis, and Lupus Nephritis), and bone diseases.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "same epitope" refers to an antibody according to the invention, characterized in inhibiting binding of antibody 1G12 to IL-18R1. An antibody is inhibited in binding to IL-18R1 if the antibody binds to the same epitope of IL-18R1 as antibody 1G12 does or is inhibited in binding to IL-18R due to steric hindrance of binding by this reference antibody Inhibition of binding between IL-18R1 and an antibody to be investigated can be detected by SPR (BIACORE) assay. The anti IL-18R1 antibody to be investigated is captured by an anti species antibody coupled to the chip surface at a concentration of 6 µg/ml (corresponds to 40 nM). Then 2.5 µg/ml IL-18R1 protein (corresponds to 20 nM IL-18R1Fcfusion) is injected at a concentration of 20 nM onto the antibody coated surface. For analysis, antibody 1G12 is added at a concentration of 50 nM onto this surface for 2 minutes and binding is measured. Upon injection, any signal reduction or no change in signal indicates that the antibody to be investigated inhibits binding of 1G12 to IL-18R1. If in addition the same result is found for the same assay wherein however antibody 1G12 is immobilized and the antibody to be investigated is added, then the antibody to be investigated binds to the "same epitope". In contrast, an increase of at least 10% in signal derived by antibody injection in at least one of both assays, shows that the antibody to be investigated does not inhibit binding of 1G12 to IL-18R1.

It is further found, that an antibody binding to the same epitope as antibody 1G12 binds, also binds to a mutated IL-18R1, wherein the mutation consists of D1-mutation SRIAL (SEQ ID NO:19) to PRVTF (SEQ ID NO:20), D1-mutation MKNYTQK (SEQ ID NO:21) to VGNDRRN (SEQ ID NO:22), D2-mutation QTLVNSTS (SEQ ID NO:23) to EELIQDTW (SEQ ID NO:24), D2-mutation NPTIKKN (SEQ ID NO:25) to TPRILKD (SEQ ID NO:26), or D2-mutation HFLHHNGKLF (SEQ ID NO:27) to FSVHHNGTRY (SEQ ID NO:28). It is further found, that an antibody binding to the same epitope as antibody 1G12 binds, does not bind to a mutated IL-18R1, wherein domain D1 and D2 are deleted. According to that was mentioned above, a signal deviation for the SPR binding to such a mutated IL-18R1 not exceeding 20% of the signal derived by binding to non mutated IL-18R1 shows that the antibody to be investigated binds also to such a mutated IL-1R1 variant.

A "Fc part" or "Fc region" of an antibody is a term well known to the skilled artisan and defined on the basis of papain cleavage of antibodies. The term defines a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th ed., Public Health Service, National Institutes of Health, Bethesda, Md. (1991). Preferably the Fc part is a human Fc part and especially preferred either from human IgG4 subclass, preferably mutated in the hinge region (e.g. S228P and/or L235E) or a mutated Fc part from human IgG1 subclass. Mostly preferred are Fc parts comprising heavy chain constant regions selected from the regions shown in SEQ ID NO:14, 15, 16, 17, and 18. Preferred light chain constant regions are shown in SEQ ID NO:12 and 13.

"Framework" or "FR" refers to variable domain residues other than hypervariable region (HVR) residues. The FR of a variable domain generally consists of four FR domains: FR1, FR2, FR3, and FR4. Accordingly, the CDR and FR sequences generally appear in the following sequence in VH (or VL): FR1-CDR1(L1)-FR2-CDR2(L2)-FR3-CDR3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, fifth ed., NIH Publication 91-3242, Bethesda Md. (1991), Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human CDRs and amino acid residues from human FRs. In certain embodiments, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" or "humanized version" or "humanized antibody" of an antibody, e.g., a non-human antibody, refers to an antibody that has undergone humanization. In one embodiment, one to all six CDRs of an antibody derived from non-human species (e.g. hamster) is (are) grafted into the framework region of a human antibody to prepare the "humanized antibody". See, e.g., Riechmann, L., et al., Nature 332 (1988) 323-327; and Neuberger, M. S., et al., Nature 314 (1985) 268-270. In one embodiment a "humanized version of an antibody" according to the invention (which is of non-human origin) refers to an antibody, which is based on the non-human antibody sequences in which the $V_H$ and $V_L$ are humanized by standard techniques (including CDR grafting) and optionally subsequent mutagenesis of certain amino acids in the framework region and the CDR. In one embodiment one to five amino acids (e.g. up to three) the framework region and/or one to three amino acids (e.g. up to two) in the CDRs can be modified by further mutations. For example the mutagenesis can be based upon molecular modeling as described by Riechmann, L., et al., Nature 332 (1988) 323-327 and Queen, C., et al., Proc. Natl. Acad. Sci. USA 86 (1989) 10029-10033, or others. The suited positions for such mutations can be identified e.g. by sequence or homology analysis, by choosing the human framework (fixed frameworks approach; homology matching or best-fit), by using consensus sequences, by selecting FRs from several different germlines, or by replacing non-human residues on the three dimensional surface with the most common residues found in human antibodies or based on sterical optimized interactions. In one embodiment such humanized version is chimerized with a human constant region.

The term "complementarity determining regions" or "CDR," as used herein, refers to each of the regions of an antibody variable domain which are hypervariable in sequence and/or form structurally defined loops ("hypervariable loops) (Kabat et al., Sequences of Proteins of Immunological Interest, 5th ed., Public Health Service, National Institutes of Health, Bethesda, Md. (1991); Chothia, C. and Lesk, A. M., J. Mol. Biol. 196 (1987) 901-917). With the exception of CDR1 in VH, CDRs generally comprise the amino acid residues that form the hypervariable loops. Generally, native four-chain antibodies comprise six CDRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary CDRs occur at amino acid residues 26-32 (L1), 50-52 (L2), 91-96 (L3), 26-32 (H1), 53-55 (H2), and 96-101 (H3). (Chothia, C. and Lesk, A. M., J. Mol. Biol. 196 (1987) 901-917) or at amino acid residues 24-34 of L1, 50-56 of L2, 89-97 of L3, 31-35B of H1, 50-65 of H2, and 95-102 of H3. (Kabat, E. A. et al., Sequences of Proteins of Immunological Interest, 5th ed. Public Health Service, National Institutes of Health, Bethesda, Md. (1991), NIH Publication 91-3242.) With the exception of CDR1 in VH, CDRs generally comprise the amino acid residues that form the hypervariable loops. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro, J. C. and Fransson, J., Front. Biosci. 13 (2008) 1619-1633). Unless otherwise indicated, CDR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example by chromatographic (e.g., ion exchange or reverse phase HPLC) methods. For review of methods for assessment of antibody purity, see, e.g., Flatman, S. et al., J. Chromatogr. B 848 (2007) 79-87).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-IL-18R1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "IL-18R1," as used herein, refers to human IL-18R1 (Interleukin-18 receptor 1, IL-18Rα, CD218 antigen-like family member A, CD218a, UniProtKB/Swiss-Prot Q13478.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt et al., Kuby Immunology, sixth ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clarkson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based on antibodies that bind to IL-18R1. Antibodies of the invention are useful, e.g., for the diagnosis or treatment of Chronic Obstructive Pulmonary Disease (COPD), inflammatory, autoimmune, rheumatoid arthritis, lupus, psoriasis or bone diseases or other IL-18R1 mediated diseases.

A. Exemplary Anti-IL-18R1 Antibodies

In a further aspect of the invention, an anti-IL-18R1 antibody according to any of the above embodiments is a monoclonal antibody, including a chimeric or humanized antibody. In one embodiment, an anti-IL-18R1 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-IL-18R1 antibody according to any of the above embodiments may incorporate any of the features, singly or in combination, as described in the sections below:

In one embodiment the humanized antibody according to the invention is characterized in comprising as heavy chain variable region CDRs a CDRH1 region of SEQ ID NO:2 or SEQ ID NO:10, a CDRH2 region of SEQ ID NO:3 and a CDRH3 region of SEQ ID NO:4, and as light chain variable region CDRs a CDRL1 region of SEQ ID NO:6, a CDRL2 region of SEQ ID NO:7 and a CDRL3 region of SEQ ID NO:8.

or a humanized version thereof.

In one embodiment the humanized antibody according to the invention is characterized in comprising as heavy chain variable region SEQ ID NO:1 and as variable light chain region SEQ ID NO:5 or as heavy chain variable region SEQ ID NO:9 and as variable light chain region SEQ ID NO:11, or a humanized version thereof.

In one embodiment the antibody according to the invention is characterized in comprising
a) as heavy chain variable region CDRs a CDRH1 region of SEQ ID NO:30, a CDRH2 region of SEQ ID NO:31 and a CDRH3 region of SEQ ID NO:32, and as light chain variable region CDRs a CDRL1 region of SEQ ID NO:34, a CDRL2 region of SEQ ID NO:35 and a CDRL3 region of SEQ ID NO:36;
b) as heavy chain variable region CDRs a CDRH1 region of SEQ ID NO:38, a CDRH2 region of SEQ ID NO:39 and a CDRH3 region of SEQ ID NO:40, and as light chain variable region CDRs a CDRL1 region of SEQ ID NO:42, a CDRL2 region of SEQ ID NO:43 and a CDRL3 region of SEQ ID NO:44;
c) as heavy chain variable region CDRs a CDRH1 region of SEQ ID NO:46, a CDRH2 region of SEQ ID NO:47 and a CDRH3 region of SEQ ID NO:48, and as light chain variable region CDRs a CDRL1 region of SEQ ID NO:50, a CDRL2 region of SEQ ID NO:51 and a CDRL3 region of SEQ ID NO:52;
d) as heavy chain variable region CDRs a CDRH1 region of SEQ ID NO:54, a CDRH2 region of SEQ ID NO:55 and a CDRH3 region of SEQ ID NO:56, and as light chain variable region CDRs a CDRL1 region of SEQ ID NO:58, a CDRL2 region of SEQ ID NO:59 and a CDRL3 region of SEQ ID NO:60; or
e) as heavy chain variable region CDRs a CDRH1 region of SEQ ID NO:62, a CDRH2 region of SEQ ID NO:63 and a CDRH3 region of SEQ ID NO:64, and as light chain variable region CDRs a CDRL1 region of SEQ ID NO:66, a CDRL2 region of SEQ ID NO:67 and a CDRL3 region of SEQ ID NO:68.

In one embodiment the antibody according to the invention is characterized in comprising
a) as heavy chain variable region SEQ ID NO:29 and as variable light chain region SEQ ID NO:33;
b) as heavy chain variable region SEQ ID NO:37 and as variable light chain region SEQ ID NO:41;
c) as heavy chain variable region SEQ ID NO:45 and as variable light chain region SEQ ID NO:49;
d) as heavy chain variable region SEQ ID NO:53 and as variable light chain region SEQ ID NO:57; or
e) as heavy chain variable region SEQ ID NO:61 and as variable light chain region SEQ ID NO:65;

1. Antibody Affinity

In certain embodiments, an antibody provided herein has a dissociation constant ($K_D$) of $10^{-8}$M or less, e.g. from $10^{-8}$M to $10^{-13}$M, e.g., from $10^{-9}$M to $10^{-13}$ M).

$K_D$ is measured using surface plasmon resonance assays using a BIACORE®-T100 or a BIACORE®-A100 (GE Healthcare, Freiburg, Germany) at 25° C. with immobilized antigen CM5 chips at 10 response units (RU). Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Antigen or a suitable capturing antibody is diluted with 10 mM sodium acetate, pH 4.8, to 5 µg/ml before injection at a flow rate of 5 µl/minute to achieve approximately 10 response units (RU) of coupled protein. Following the injection of protein, 1 M ethanolamine is injected to block unreacted groups. Prior the binding event to be measured one binding partner is already immobilized onto the surface or was captured by a suitable capturing system (e.g. human IgG specific antibodies to capture human IgGs). For kinetic measurements, two-fold serial dilutions of Fab/antibody/antigen (0.78 nM to 500 nM) are injected in PBS with 0.05% polysorbate 20 (TWEEN-20™) surfactant (PBST) at 25° C. at a flow rate of approximately 30 µl/min. After the binding event the surface was regenerated for the next cycle. Association rates ($k_a$) and dissociation rates ($k_d$) are calculated using a simple one-to-one Langmuir binding model (BIACORE® Evaluation Software version 4.1) by simultaneously fitting the association and dissociation curve. The equilibrium dissociation constant ($K_D$) is calculated as the ratio $k_d/k_a$. See, e.g., Chen, Y. et al., J. Mol. Biol. 293 (1999) 865-881. If $k_a$ exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, In: The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (2003) 129-134.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for IL-18R1 and the other is for any other antigen. In certain embodiments, bispecific antibodies may bind to two different epitopes of IL-18R1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553); using "diabody" technology for making bispecific antibody fragments (see, e.g., Holliger, P. et al., Proc. Natl. Acad. Sci. USA, 90 (1993) 6444-6448); and using single-chain Fv (sFv) dimers (see, e.g. Gruber, M. et al., J. Immunol., 152 (1994) 5368-5374); and preparing trispecific antibodies as described, e.g., in Tutt, A. et al., J. Immunol. 147 (1991) 60-69.

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to IL-18R1 as well as another, different antigen (see, US 2008/0069820, for example).

4. Antibody Variants a) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region (see, e.g., Wright, A. et al., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063) and Hellstrom, I. et al., Proc. Natl. Acad. Sci. USA 82 (1985) 1499-1502; U.S. Pat. No. 5,821,337 (see Brueggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes, R. et al. Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (19969 163-171; Cragg, M. S. et al., Blood 101 (2003) 1045-1052; and Cragg, M. S. and M. J. Glennie, Blood 103 (2004) 2738-2743). FcRn binding and in vivo clearance/half life determinations can also be performed using methods known in the art (see, e.g., Petkova, S. B. et al., Intl. Immunol. 18 (2006) 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737, 056; WO 2004/056312, and Shields, R. L. et al., J. Biol. Chem. 276 (2001) 6591-6604.)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371, 826).

See also Duncan, A. R. and Winter, G., Nature 332 (1988) 738-740; U.S. Pat. No. 5,648,260; U.S. Pat. No. 5,624,821; and WO 94/29351 concerning other examples of Fc region variants.

c) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

d) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-IL-18R1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-IL-18R1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-IL-18R1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see also Charlton, K. A., In: Methods in Molecular Biology, Vol. 248, Lo B. K. C. (ed.), Humana Press, Totowa, N.J. (2003), pp. 245-254, describing expression of antibody fragments in *E. coli*). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414, and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. J. et al., Methods in Molecular Biology 248 (2003) 255-268.

C. Methods and Compositions for Diagnostics and Detection

In certain embodiments, any of the anti-IL-18R1 antibodies provided herein is useful for detecting the presence of IL-18R1 in a biological sample. The term "detecting" as used herein encompasses quantitative or qualitative detection. In certain embodiments, a biological sample comprises a cell or tissue, such as tumor tissue.

In one embodiment, an anti-IL-18R1 antibody for use in a method of diagnosis or detection is provided. In a further aspect, a method of detecting the presence of IL-18R1 in a biological sample is provided. In certain embodiments, the method comprises contacting the biological sample with an anti-IL-18R1 antibody as described herein under conditions permissive for binding of the anti-IL-18R1 antibody to IL-18R1, and detecting whether a complex is formed between the anti-IL-18R1 antibody and IL-18R1. Such method may be an in vitro or in vivo method. In one embodiment, an anti-IL-18R1 antibody is used to select subjects eligible for therapy with an anti-IL-18R1 antibody, e.g. where IL-18R1 is a biomarker for selection of patients.

Exemplary disorders that may be diagnosed using an antibody of the invention are Chronic Obstructive Pulmonary Disease (COPD), inflammatory, autoimmune, rheumatoid arthritis, lupus, psoriasis or bone diseases.

In certain embodiments, labeled anti-IL-18R1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Pharmaceutical Formulations

Pharmaceutical formulations of an anti-IL-18R1 antibody as described herein are prepared by mixing such antibody having the desired degree of purity with one or more optional pharmaceutically acceptable carriers (Remington's Pharmaceutical Sciences, 16th ed., Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th ed., Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

E. Therapeutic Methods and Compositions

Any of the anti-IL-18R1 antibodies provided herein may be used in therapeutic methods.

In one aspect, an anti-IL-18R1 antibody for use as a medicament is provided. In further aspects, an anti-IL-18R1 antibody for use in treating Chronic Obstructive Pulmonary Disease (COPD), inflammatory, autoimmune, rheumatoid arthritis, lupus, psoriasis or bone diseases or other IL-18R1 mediated diseases is provided. In certain embodiments, an anti-IL-18R1 antibody for use in a method of treatment is provided. In certain embodiments, the invention provides an anti-IL-18R1 antibody for use in a method of treating an individual having Chronic Obstructive Pulmonary Disease (COPD), inflammatory, autoimmune, rheumatoid arthritis, lupus, psoriasis or bone disease comprising administering to the individual an effective amount of the anti-IL-18R1 antibody. In one such embodiment, the method further comprises administering to the individual an effective amount of at least one additional therapeutic agent, e.g., as described below. In further embodiments, the invention provides an anti-IL-18R1 antibody for use in blocking interaction between IL-18 and the receptors IL-18R1 and IL18RAP, Uniprot Accession No. O95256, and inhibiting IL-18 receptor mediated signaling and NFkappaB pathway activation. The NFkappaB pathway and its activation (signaling) is e.g. described in Kearns J. D. and Hoffmann, A., J. Biol. Chem. 284 (2009) 5439-5443. An "individual" according to any of the above embodiments is preferably a human.

In a further aspect, the invention provides for the use of an anti-IL-18R1 antibody in the manufacture or preparation of a medicament. In one embodiment, the medicament is for treatment of Chronic Obstructive Pulmonary Disease (COPD), inflammatory, autoimmune, rheumatoid arthritis, lupus, psoriasis or bone disease. In a further embodiment, the medicament is for use in a method of treating Chronic Obstructive Pulmonary Disease (COPD), inflammatory, autoimmune, rheumatoid arthritis, lupus, psoriasis or bone disease comprising administering to an individual having Chronic Obstructive Pulmonary Disease (COPD), inflammatory, autoimmune, rheumatoid arthritis, lupus, psoriasis or bone disease an effective amount of the medicament. In one such embodiment, the method further comprises administering to the individual an effective amount of at least one additional therapeutic agent, e.g., as described below. In a further embodiment, the medicament is useful for blocking interaction between IL-18 and the receptors IL-18R1 and IL18RAP, Uniprot Accession No. O95256, and inhibiting IL-18 receptor mediated signaling and NFkappaB pathway activation in an individual. An "individual" according to any of the above embodiments may be a human.

In a further aspect, the invention provides a method for treating a Chronic Obstructive Pulmonary Disease (COPD), inflammatory, autoimmune, rheumatoid arthritis, lupus, psoriasis or bone disease. In one embodiment, the method comprises administering to an individual having such Chronic Obstructive Pulmonary Disease (COPD), inflammatory, autoimmune, rheumatoid arthritis, lupus, psoriasis or bone disease an effective amount of an anti-IL-18R1 antibody. In one such embodiment, the method further comprises administering to the individual an effective amount of at least one additional therapeutic agent, as described below. An "individual" according to any of the above embodiments may be a human.

Preferably the antibody according to the invention blocks interaction between IL-18 and the receptors IL-18R1 and IL18RAP, Uniprot Accession No. O95256, and inhibits IL-18 receptor mediated signaling and NFkappaB pathway activation. Such an antibody is antibody 1G12 or antibody 2D11. In one embodiment, the method comprises administering to the individual an effective amount of an anti-IL-18R1 antibody. In one embodiment, an "individual" is a human.

In a further aspect, the invention provides pharmaceutical formulations comprising any of the anti-IL-18R1 antibodies provided herein, e.g., for use in any of the above therapeutic methods. In one embodiment, a pharmaceutical formulation comprises any of the anti-IL-18R1 antibodies provided herein and a pharmaceutically acceptable carrier. In another embodiment, a pharmaceutical formulation comprises any of the anti-IL-18R1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering about 4 to 10 mg/kg. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-IL-18R1 antibody.

F. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-IL-18R1 antibody.

III. Description of the Sequence Listing

SEQ ID NO:1 heavy chain variable region (VH) of Mab1G12
SEQ ID NO:2 heavy chain CDRH1 Mab1G12
SEQ ID NO:3 heavy chain CDRH2 Mab1G12
SEQ ID NO:4 heavy chain CDRH3 Mab1G12
SEQ ID NO:5 light chain variable region (VL) of Mab1G12
SEQ ID NO:6 light chain CDRL1 Mab1G12
SEQ ID NO:7 light chain CDRL2 Mab1G12
SEQ ID NO:8 light chain CDRL3 Mab1G12
SEQ ID NO:9 heavy chain variable region (VH) of Mab2D11
SEQ ID NO:10 heavy chain CDRH1 Mab2D11
SEQ ID NO:3 heavy chain CDRH2 Mab2D11
SEQ ID NO:4 heavy chain CDRH3 Mab2D11
SEQ ID NO:11 light chain variable region (VL) of Mab2D11
SEQ ID NO:6 light chain CDRL1 Mab2D11
SEQ ID NO:7 light chain CDRL2 Mab2D11
SEQ ID NO:8 light chain CDRL3 Mab2D11
SEQ ID NO:12 Human kappa light chain
SEQ ID NO:13 Human lambda light chain
SEQ ID NO:14 Human IgG1 (Caucasian Allotype)
SEQ ID NO:15 Human IgG1 (Afroamerican Allotype)
SEQ ID NO:16 Human IgG1 LALA-Mutant (Caucasian Allotype)
SEQ ID NO:17 Human IgG4
SEQ ID NO:18 Human IgG4 SPLE-Mutant
SEQ ID NO:19 to 28: fragments and mutant fragments of IL-18Rα
SEQ ID NO:29 heavy chain variable region (VH) of humanized Mab1G12-9.6
SEQ ID NO:30 heavy chain CDRH1 humanized Mab1G12-9.6
SEQ ID NO:31 heavy chain CDRH2 humanized Mab1G12-9.6
SEQ ID NO:32 heavy chain CDRH3 humanized Mab1G12-9.6
SEQ ID NO:33 light chain variable region (VL) of humanized Mab1G12-9.6
SEQ ID NO:34 light chain CDRL1 humanized Mab1G12-9.6
SEQ ID NO:35 light chain CDRL2 humanized Mab1G12-9.6
SEQ ID NO:36 light chain CDRL3 humanized Mab1G12-9.6
SEQ ID NO:37 heavy chain variable region (VH) of humanized Mab1G12-10.5
SEQ ID NO:38 heavy chain CDRH1 humanized Mab1G12-10.5
SEQ ID NO:39 heavy chain CDRH2 humanized Mab1G12-10.5

SEQ ID NO:40 heavy chain CDRH3 humanized Mab1G12-10.5

SEQ ID NO:41 light chain variable region (VL) of humanized Mab1G12-10.5

SEQ ID NO:42 light chain CDRL1 humanized Mab1G12-10.5

SEQ ID NO:43 light chain CDRL2 humanized Mab1G12-10.5

SEQ ID NO:44 light chain CDRL3 humanized Mab1G12-10.5

SEQ ID NO:45 heavy chain variable region (VH) of humanized Mab1G12-10.6

SEQ ID NO:46 heavy chain CDRH1 humanized Mab1G12-10.6

SEQ ID NO:47 heavy chain CDRH2 humanized Mab1G12-10.6

SEQ ID NO:48 heavy chain CDRH3 humanized Mab1G12-10.6

SEQ ID NO:49 light chain variable region (VL) of humanized Mab1G12-10.6

SEQ ID NO:50 light chain CDRL1 humanized Mab1G12-10.6

SEQ ID NO:51 light chain CDRL2 humanized Mab1G12-10.6

SEQ ID NO:52 light chain CDRL3 humanized Mab1G12-10.6

SEQ ID NO:53 heavy chain variable region (VH) of humanized Mab1G12-11.6

SEQ ID NO:54 heavy chain CDRH1 humanized Mab1G12-11.6

SEQ ID NO:55 heavy chain CDRH2 humanized Mab1G12-11.6

SEQ ID NO:56 heavy chain CDRH3 humanized Mab1G12-11.6

SEQ ID NO:57 light chain variable region (VL) of humanized Mab1G12-11.6

SEQ ID NO:58 light chain CDRL1 humanized Mab1G12-11.6

SEQ ID NO:59 light chain CDRL2 humanized Mab1G12-11.6

SEQ ID NO:60 light chain CDRL3 humanized Mab1G12-11.6

SEQ ID NO:61 heavy chain variable region (VH) of humanized Mab1G12-12.6

SEQ ID NO:62 heavy chain CDRH1 humanized Mab1G12-12.6

SEQ ID NO:63 heavy chain CDRH2 humanized Mab1G12-12.6

SEQ ID NO:64 heavy chain CDRH3 humanized Mab1G12-12.6

SEQ ID NO:65 light chain variable region (VL) of humanized Mab1G12-12.6

SEQ ID NO:66 light chain CDRL1 humanized Mab1G12-12.6

SEQ ID NO:67 light chain CDRL2 humanized Mab1G12-12.6

SEQ ID NO:68 light chain CDRL3 humanized Mab1G12-12.6

SEQ ID NO:69 light chain CDRL1 consensus sequence

SEQ ID NO:70 light chain CDRH1 consensus sequence

SEQ ID NO:71 light chain CDRH2 consensus sequence

SEQ ID NO:72 human IL-18R1 (IL-18Rα)

EXAMPLES

The following are examples of methods and compositions of the invention. It is understood that various other embodiments may be practiced, given the general description provided above.

Example 1

Immunization 8-10 weeks old NMRI mice were used for immunization. Immunization was performed via DNA vaccination. Briefly 30 ul of water dissolved DNA plasmid expressing both chains (alpha and beta) of human IL-18 receptor was injected intradermally into the back of isoflurane-anaesthetized mice immediately prior to electroporation. Immunization was performed every 2 weeks without any adjuvant. The mice were bled periodically to determine if an adequate antibody response had developed. For this purpose blood was collected from the retro-orbital sinus and serum was tested in an IL-18Rα specific ELISA as well as in a functional KG-1/IFNgamma assay and in Biacore for selection of an appropriate animal for fusion. Mice were given an intravenous antigen boost 4 days before harvesting spleens to activate B cells and increase the number of antigen positive cells located in the spleen. Spleens were collected from adequately immunized mice just prior to the fusion to myeloma cells.

Example 2

Inhibition of huIL-18 Binding to IL-18RαB Complex (ELISA)

The test was performed on 384 well microtiter plates at room temperature (RT). After each incubation step plates were washed 3 times with PBST (Phosphate Buffered Saline Tween®-20). At the beginning, plates were coated with 0.5 µg/ml goat anti-human IgG Fc fragment (Jackson 1 mm. Res., US, Cat. No. 109-006-170) for at least 2 hours (h). Thereafter the wells were blocked with PBS supplemented with 0.1% Tween®-20 and 2% BSA (Roche Diagnostics GmbH, DE) for 1 h. 0.2 µg/ml of recombinant human IL-18Rα Fc chimera (R&D Systems, UK, Cat. No. 816-LR) was captured for 1 h. Dilutions of purified antibodies in PBS with 0.5% BSA and 0.05% Tween®-20 were incubated with the receptor protein for 1 h. Biotinylated human IL-18 (MBL International, US, Cat. No. B003-5) and 0.2 µg/ml IL-18R13 (R&D Systems, UK, Cat. No. 118-AP) were added for an additional hour to build up the trimeric complex. IL-18 was biotinylated with Sulfo-NHS-LC-Biotin (Thermo Scientific Pierce, US, Cat. No. 21327) according to the manufacturer's protocol and purified using Zeba™ Desalt Spin Column (Thermo Scientific Pierce, US, Cat. No. 89889). Binding of the biotinylated IL-18 to the complex was detected with 1:2000 diluted streptavidin HRP (Roche Diagnostics GmbH, DE, Cat. No. 11089153001). After 1 h the plates were washed 6 times with PBST and developed with freshly prepared BM Blue® POD substrate solution (BM Blue®: 3,3'-5,5'-Tetramethylbenzidine, Roche Diagnostics GmbH, DE, Cat. No. 11484281001) for 30 minutes at RT. Absorbance was measured at 370 nm. The negative control was defined without addition of IL-18Rα protein and the positive control was defined with all components but without antibody. The commercially available anti-human IL-18Rα murine MAb Clone 70625 (R&D Systems #MAB840) was used for comparison. Results are shown in table 1:

TABLE 1

| Antibody | IC50 (µg/mL) | IC50 (nM) |
|---|---|---|
| F20.1G12 | 0.022 | 0.15 |
| F20.2D11 | 0.029 | 0.19 |
| Mab 840 | 0.044 | 0.29 |

IL-18Rβ: human IL-18 receptor accessory protein, IL-18RAP (Uniprot Accession No. O95256)

Example 3

IL-18 Induced IFNγ Production by Human KG-1 Cells a) Reagents:
  KG1 cell line (ATCC#CCL246)
  Culture medium: RPMI 1640 supplemented with 10% FCS with Pen/Strep
  Recombinant Human IL-18 (RnD systems #B003-2)
  BD OptEIA Human IFNγ ELISA Set (BD #555142)
  rhTNFalpha (R&D cat 210-TA)
b) Procedure:
KG-1 cells were grown in RPMI 1640 supplemented with 10% FCS and Pen/Strep in a 5% $CO_2$/95% air mixture at 37° C. Cells were passaged when they reached a density of $2 \times 10^6$ cells/ml and diluted to a density of $4 \times 10^5$ cells/ml. To determine the effective concentration for IL-18, KG-1 cells were resuspended at $1 \times 10^6$ cells/ml and 100 µl/well in 96-well plate in growth medium with various dose of rhIL-18 (0-200 ng/ml), supernatants were collected for IFNγ ELISA analysis. Antibodies were preincubated with KG-1 cells at $1 \times 10^6$ cells/ml and 100 µl/well in 96-well plate in growth medium for 60 mins (final concentrations between 1 ng/ml and 10 ug/ml), rhIL-18 (10 ng/ml) and TNFalpha (5 ng/ml) were added to the culture and incubated for 16-20 h at 37° C. Supernatants were collected for IFNγELISA analysis. KG-1 cells were stimulated over night with 10 ng/ml TNFalpha to induce IL18R expression. Cells were then incubated with anti-IL18R-antibodies for different time periods, followed by a) detection of bound antibody or b) determination of IL18R surface expression. Results are shown in table 2. Anti IL-18Ra Mab 840 (R&D Systems), e.g., showed an $IC_{50}$ [pM]-value of 798 pM.

TABLE 2

| Antibody | $IC_{50}$ [pM] |
|---|---|
| Mab1G12 | 27 |
| Mab2D11 | 43 |

Example 4

Determination of the Affinity of Anti-IL-18Rα Antibodies to Full Length hIL-18Rα (hFc Chimera)

Instrument: BIACORE® A100
Chip: CM3 (GE Healthcare BR-1006-36)
Coupling: amine coupling
Buffer: 1×PBS (10×PBS, Ambion cat. AM9625), pH 7.4, 37° C.

For affinity measurements 10 µg/ml anti-mouse Fcγ antibodies (from goat, Jackson Immuno Reasearch JIR115-005-071) or 10 µg/ml anti-human Fcγ antibodies (from goat, Jackson Immuno Reasearch JIR109-005-098) have been coupled to the chip surface for capturing the antibodies against hIL-18Rα. hIL-18Rα (hFc-chimera R&D-Systems 816-LR) was added in various concentrations in solution containing 0.1% BSA (Roche Ref 10238040001). Association was measured by a hIL-18Rα-injection of 1.5 minutes at 37° C.; dissociation was measured by washing the chip surface with buffer for 10 minutes at 37° C. For calculation of apparent $K_D$ and other kinetic parameters the Langmuir 1:1 model was used. Results are shown in table 3.

TABLE 3

Affinity data measured by SPR (BIACORE® T100) at 37° C.

| Antibody | App. $K_D$ (M) | $k_a$ (1/Ms) | $k_d$ (1/s) | $t_{1/2}$ (min) |
|---|---|---|---|---|
| Mab 1G12 | $2.7 \times 10^{-11}$ | $8.2 \times 10^6$ | $2.0 \times 10^{-4}$ | 58 |
| Mab 2D11 | $2.7 \times 10^{-11}$ | $7.0 \times 10^6$ | $1.9 \times 10^{-4}$ | 62 |
| MS | $6.4 \times 10^{-11}$ | $5.1 \times 10^6$ | $3.0 \times 10^{-4}$ | 39 |

MS: antibody of SEQ ID NO:3 and 4 of WO 2007096396.

Example 5a

Cross-Competition by Utilizing Surface Plasmon Resonance (SPR)

Instrument: BIACORE® A100
Chip: CM5 (Biacore BR-1006-68)
Coupling: amine coupling
Buffer: 1×PBS (10×PBS, Ambion cat. AM9625), pH 7.4, 25° C.

For epitope mapping assays via cross-competition 30 µg/ml anti-mouse Fcγ antibodies or anti-human Fcγ antibodies (from goat, Jackson Immuno Research Cat. No. 115-005-071 and Cat. No. 109-005-098) were coupled to sensor chip surface for presentation of the antibody against hIL-18Rα. After capture of 1-6 µg/ml anti-hIL-18Rα monoclonal antibodies free binding capacities of capture antibodies was blocked for 4 min with 250 µg/ml mouse or human immunoglobulins (Jackson Immuno Research 015-000-003 or 009-000-003) followed by injection of 2.5 µg/ml hIL-18Rα (hFc-chimera R&D-Systems Cat. No. 816-LR) for 2 min. Binding of 0.6-3 µg/ml second anti-hIL-18Rα antibody was analyzed by injection for 2 min, dissociation was measured by washing with buffer for 2 minutes. The assay and the measurements were conducted at 25° C. The specific binding of the second anti-hIL-18Rα antibody was referenced against the same chip setup up but only without injection of hIL-18R. The cross competition data was calculated as a percentage (%) of expected binding response of the second anti-hIL-18Rα antibody. The item "percentage (%) of expected binding response" for binding of the second antibody was calculated by "100*relative response (sample_stability_late)/rMax", where rMax is calculated by "relative response of antigen (general_stability_late)*antibody molecular weight/antigen molecular weight" as described in Biacore epitope mapping instructions (for BIACORE® A100 instrument). Results are shown in Table 4a.

TABLE 4a

Percentage of expected binding response for antibody 2

| Antibody 1 | Antibody 2 | | |
|---|---|---|---|
| | Mab 1G12 | Mab 2D11 | MS |
| Mab1G12 | 0 | 0 | 52 |
| Mab2D11 | 0 | 0 | 48 |
| MS | 76 | 76 | 0 |

MS: antibody of SEQ ID NO:3 and 4 of WO 2007096396.

A binding between 1G12 and 2D11 is not detectable, as they bind within the same epitope cluster, whereas binding of 'MS' is detectable (listed in (%) of expected binding response of the second anti-hIL-18Rα antibody) showing that 'MS' binds to another epitope cluster than 1G12 and 2D11. As well binding of 'MS' is not detecable when 'MS' is prebound.

In a second experiment the binding of the antibodies according to the invention was compared to Anti-IL-18Ralpha Mab 840 (R&D Systems). Results are shown in Table 4b.

TABLE 4b

Percentage of expected binding response for antibody 2

| Antibody 1 | Antibody 2 | | |
|---|---|---|---|
| | F20.1G12 | F20.2D11 | Mab840 |
| Mab1G12 | 5 | 5 | 97 |
| Mab2D11 | 5 | 5 | 97 |
| Mab840 | 119 | 121 | 13 |

Binding between 1G12 and 2D11 is not detectable, as they bind within the same epitope, whereas Mab 840 binds to a different epitope than 1G12 and 2D11.

Figure 2:
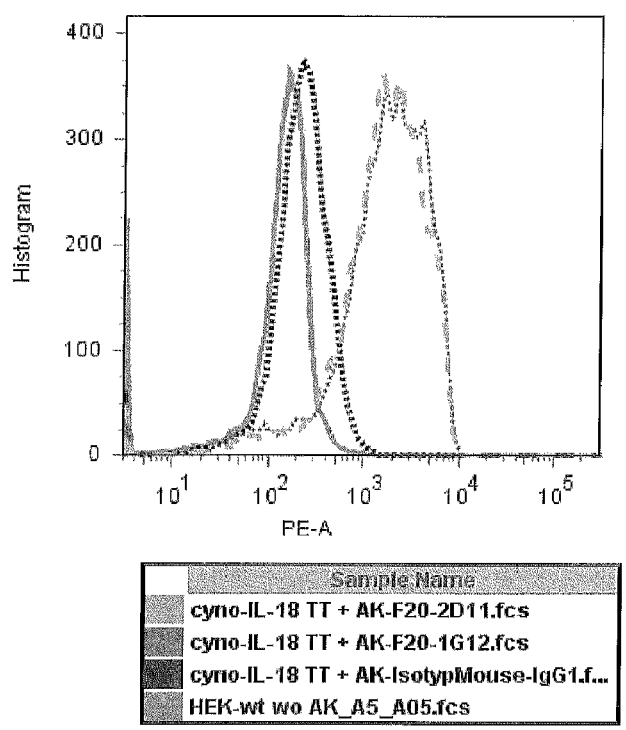
FIG. 2: FACS against cynomolgus IL-18Rα/IL-18R13 transfected HEK293 cells.

Example 6 a) FACS Assay on Human IL-18Rα/IL-18Rβ Transfected HEK293 Cells $10^6$ HEK293 cells were transfected with a plasmid expressing human IL-18Ralpha+IL-18Rβ. Transfected cells were incubated for 1 day. $1 \times 10^5$ cells were incubated on ice in PBS-buffer+2% FCS and stained with an IL-18Rα antibody (1 μg/ml). As secondary antibody anti-mouse IgG1-PE from R&D Systems (F0102B) was added in 1:20 dilution and as isotype control mouse IgG1 from BD Pharmingen (557273) was used at a concentration of 1 μg/ml. Results in FIG. 1 show that antibodies 1G12 (F20.1G12) and 2D11 ((F20.2D11) both bind to cells transfected and expressing human IL-18Ralpha+IL-18Rβ subunits.

b) FACS Assay on Cynomolgus IL-18Rα/IL-18Rβ Transfected HEK293 Cells $10^6$ HEK293 cells were transfected with a plasmid expressing cynomolgus IL-18Ralpha+IL-18R13. Transfected cells were incubated for 1 day. $10^5$ cells were incubated on ice in PBS-buffer+2% FCS and stained with a Mab_IL-18Rα antibody at a concentration of 1 μg/ml. As secondary antibody anti-mouse IgG1-PE from R&D Systems (F0102B) was added in 1:20 dilution and as isotype control mouse IgG1 from BD Pharmingen (557273) was used at a concentration of 1 μg/ml. Results in FIG. 2 show that antibodies 1G12 (F20.1G12) and 2D11 ((F20.2D11) both bind to cells transfected and expressing cynomolgus IL-18Ralpha+IL-18Rβ subunits.

Example 7

Cellular ELISA on CHO Cells Expressing Cynomolgus IL-18Ralpha or Cynomolgus IL-18Ralpha and Beta The recombinant cell lines CHO-K1 expressing cynomolgus IL-18Rα or cynomolgus IL-18Rα+β were stained with the Mab_IL-18R antibodies in a cell ELISA. Controls are CHO-K1 untransfected cells. Cells were grown in F-12 medium (GIBCO) with Glutamax-1 (GIBCO Cat. No. 31331-028)+10% FCS (PAN Cat. No. 2802-P920707). For cultivation of the recominant cell lines 250 μg/ml G418 (Geneticin, GIBCO, Cat. No. 10131-019) was added. As control antibody anti hIL-18Ralpha Antibody Mab840 (Mouse monoclonal IgG1 from R&D Systems, Cat. MAB 840) and as detection antibody goat anti-mouse IgG (H+L)-HRP conjugate (BioRad) was added. For running the assay, on day 1 $2 \times 10^4$ CHO_CynoIL-18Rα, CHO_CynoIL-18Rα+β or untransfected CHO cells in 50 μl F-12/well were seeded in a 96-well plate and incubated overnight at 37° C. On day 2, 50 μl supernatant or (2×) purified antibody diluted in medium or 50 μl Hybridoma supernatant were added and incubated for 2 h at 4° C. Supernatant was aspirated and 100 μl/well Glutaraldehyde fixing solution (25% stock solution Grade EM; final concentration=0.05% in PBS) was added and incubated for 10 minutes at room temperature. For washing 2 times 200 μl PBS/well/wash was added and removed. 50 μl of ELISA detection-antibody diluted in ELISA blocking reagent (ELISA blocking stock reagent diluted 1:10 in PBS) was added. Goat anti-mouse IgG (H&L)-HRP conjugate diluted 1:2000 was added and incubated for 2 h at room temperature on a shaker. Solution was aspirated and washing was performed 3 times with 200 μl PBS/well/wash. 50 μl TMB was added for 7-10 min. (until blue color develops). The reaction was stopped by addition of 25 μM $H_2SO_4$. The plates were measured at 450 nm-620 nm using an ELISA reader (TECAN). Results are shown in Table 5. No binding was observed with the untransformed cells.

TABLE 5

| Antibody | CHO CyIL-18Rα $EC_{50}$ (ng/ml) | CHO CyIL-18Rα + β $EC_{50}$ (ng/ml) |
|---|---|---|
| Mab 1G12 | 18.58 | 15.01 |
| 'Reg' | 185.44 | 139.46 |
| 'MS' | ≥1000.00 | ≥1000.00 |

It is important for Tox investigation and for PK/PD assay that the antibody recognize Cyno IL-18Rα with similar EC50 as compared to its binding to human IL-18Rα.

Example 8

Investigation of IL-18 Induced IFNγ Production in Human PBMC

IL-18 has a biological function in Natural killer (NK) and TH1 cell activation, e.g. by induction of Interferon-gamma (IFNγ) in CD4+ and other T cells, B cells, NK cells and Monocytes. IL-18 also synergizes with IL-12 in inducing IFNγ in human T cells (w/o TCR engagement) similar to IL-1β (Tominaga, K. et al., Int. Immunol. 12 (2000) 151-160).

Hereby the mechanism is linked to the IL-12-induced expression of IL-18Rα chain as described for TH1 but not TH2 cells. To assess the functional impact of anti-IL-18 mAbs, both against the receptor and the ligand, peripheral Blood Mononuclear Cells were isolated by standard Ficoll Paque technique. $2 \times 10^5$ cells/well were pre-cultured in 96 flat-bottom-wells (200 µl volume) in the presence of 5 ng/ml IL-12 (Sigma) for 3 days. Then, IL-18 (MBL, http://www.mblintl.com/) was added at a final concentration of 10 ng/ml for 3 additional days. To block either the receptor or neutralize the ligand anti-IL18 or anti-IL-18R mAbs were added at a final concentration of 0.01-0.5/1.0 µg/ml at this point. After a total of 6 days, the IFNγ production in the supernatent was analyzed by ELISA. Results are shown in Table 6.

TABLE 6

| Antibody | $IC_{50}$ [ng/ml] |
|---|---|
| Mab 1G12 | 0.76 ± 0.5 |
| Mab 2D11 | 1.71 ± 0.3 |
| Reg | 2.3 ± 3.2 |
| MS | 2.6 ± 2.4 |

Example 9

Binding of Antibodies to huIL-18Rα and other IL-1 Receptor Family Proteins (ELISA)

The test was performed on 384-well microtiter plates (MaxiSorp™, Thermo Scientific Nunc, DK, Cat. No. 464718) at RT. After each incubation step, plates were washed 3 times with PBST. At the beginning, plates were coated with 0.5 µg/ml goat anti-human IgG Fc fragment (Jackson 1 mm. Res., US, Cat. No. 109-006-170) for at least 2 hours (h). Thereafter the wells were blocked with PBS supplemented with 0.2% Tween®-20 and 2% BSA (Roche Diagnostics GmbH, DE) for 1 h. 0.2 µg/ml of recombinant human IL-18Rα-Fc fusion protein (R&D Systems, UK, Cat. No. 816-LR) was captured on plate for 1 h. For testing the binding of antibodies to other proteins of the IL-1 receptor family 0.2 µg/ml of the following recombinant human proteins conjugated to human Fc (hFc) were captured:

rhIL-1RI/hFc (R&D Systems, UK, Cat. No. 269-1R)
rhIL-1sRII/hFc (R&D Systems, UK, Cat. No. 263-2R)
rhIL-1R3/hFc (R&D Systems, UK, Cat. No. 676-CP)
rhIL-2Rα/hFc (R&D Systems, UK, Cat. No. 1020-RL)
rhIL-7Rα/hFc (R&D Systems, UK, Cat. No. 306-IR)
rhIL-15R/hFc (R&D Systems, UK, Cat. No. 147-IR)
rhST-2/hFc (R&D Systems, UK, Cat. No. 523-ST)

After washing the plate, dilutions of purified antibodies in PBS with 0.05% BSA and 0.2% Tween®-20 were incubated with the receptor proteins for 1 h. Binding of antibodies was detected with 1:2000 diluted horseradish peroxidase (HRP)-conjugates of anti-mouse IgG (GE Healthcare, UK, Cat. No. NA9310V). After 1 h the plates were washed 6 times with PBST and developed with freshly prepared BM Blue® POD substrate solution (BM Blue®: 3,3"-5,5"-Tetramethylbenzidine, Roche Diagnostics GmbH, DE, Cat. No. 11484281001) for 30 minutes at RT. Absorbance was measured at 370 nm. The values were corrected for the control without antibody. Results are shown in Table 7.

TABLE 7

("/rhIL-1RI" means "rhIL-1RI/hFc" etc.)

| Antibody | rhIL-1RI | rhIL-1sRII | rhIL-1R3 | rhIL-2Rα | rhIL-7Rα | rhIL-15R | rhST-2 | rhIL-18Rα |
|---|---|---|---|---|---|---|---|---|
| Mab1G12 | 0.01 | −0.03 | 0.00 | −0.01 | −0.01 | 0.04 | −0.01 | 2.43 |
| Mab2D11 | 0.02 | −0.05 | 0.02 | 0.02 | −0.01 | 0.19 | 0.02 | 2.56 |

Example 10

Receptor Internalization

KG-1 cells were stimulated overnight with 10 ng/ml TNFalpha to induce IL18R expression. Cells were then incubated with anti-IL18R-antibodies for different time periods, followed by a) detection of bound antibody or b) determination of IL18R surface expression. None of the tested antibodies according to the invention (2D11, 1G12) induced receptor internalization or downregulation.

Example 11

Human $TH_1$-Assay

Peripheral blood mononuclear cells (PBMC) were isolated from healthy volunteers by a Ficoll Hypaque density gradient. After washing the cells with RPMI they were resuspended in PBS, pH 7.2, with 0.5% BSA and 2 mM EDTA. T cells were isolated from PBMC using Pan T cell isolation kit (Miltenyi biotec) and magnetic separation by AutoMACS™ separator. The enriched T cells were washed 3 times using completed RPMI 1640 (supplemented with 10% FCS, 2-mercaptoethanol, L-glutamine, HEPES buffer, sodium pyruvate and Pen/Strep) resuspended and plated at $1 \times 10^6$ cells/ml in 6-well flat bottom plates coated with 2 µg/ml anti-CD3 incubated for 4 days at 37° C. with 1 ug/ml soluble anti-CD28 (BD Biosciences), 10 ng/ml of IFN-γ, 30 ng/ml of IL-12 and 10 ug/ml of anti-IL-4 (Peprotech). Then, cells were washed with complete RPMI 2 times and then rested at $2 \times 10^6$ cells/ml in complete RPMI with recombinant IL-2 (50 unit/ml). Cells were subsequently treated with serial diluted anti-IL-18Rα Ab or isotype control Ab (0-1 ug/ml) for 30 min, then restimulated with 10 ng/ml of IL-18, 2 ng/ml of IL-12 (Peprotech), at $1 \times 10^5$ cells per well, cultured in 96-well flat bottom plates at 37° C. under 5% $CO_2$ overnight. Supernatants were collected for IFN-γ ELISA analysis using BD OptEIA human IFN-γ ELISA set (Cat#555142). (BD Biosciences). Absorbance was read using Spectromax microplate reader and the data was analyzed using PRISM (GraphPad Software). Results are shown in table 8a.

TABLE 8a

| Antibody | human $TH_1$-assay $IC_{90}$ [pM] |
|---|---|
| Mab1G12 | 76.2 |
| Mab2D11 | 87.1 |
| 'MS' | 2914.5 |
| Reg | 2832.0 |

Th1/Tc1 and Th2/Tc2 imbalances are implicated in the pathogenesis of chronic obstructive pulmonary disease (COPD), Th1/Tc1 cells expresses high level of IL-18Rα, and peripheral T cell function correlates with severity of COPD (Zhu, X. et al., J. Immunol. 182 (2009) 3270-3277; Freeman, C. M. et al., J. Immunol. 184 (2010) 6504-6513; Shirai, T. et al., Allergol. Int. 59 (2010) 75-82). This assay focuses on T cells, whereby T cells were activated and cultured in Th1 conditions and they express high level of IL-18Rα, therefore this assay requires the highest amount of anti-IL-18Rα Ab for neutralization. The antibodies according to the invention show improved $IC_{90}$ values in this human TH1-assay and are therefore valuable compounds for the treatment of TH1 dependent diseases.

In a second experiment the $IC_{90}$ values in this human TH1-assay for the humanized antibodies was determined. Results are shown in Table 8b.

TABLE 8b

| Antibody | human $TH_1$-assay $IC_{90}$ [pM] |
|---|---|
| Mab1G12-9.6 | 148.4 |
| Mab1G12-10.5 | 283.2 |
| Mab1G12-10.6 | 93.5 |
| Mab1G12-11.6 | 77.0 |
| Mab1G12-12.6 | 399.4 |
| 'MS' | 1431.57 |
| Reg | 2361.87 |

Also the humanized antibodies according to the invention show improved $IC_{90}$ values in this human TH1-assay and are therefore valuable compounds for the treatment of such diseases.

Example 12

Description of the Primary Human COPD Whole Blood Assay

Peripheral blood from healthy non-smokers and patients with COPD (Gold stage II-IV) were collected in sodium heparin tubes, treated with serial diluted anti-IL-18Rα antibody or isotype control Ab (0-0.5 ug/ml) for 30 min, then stimulated with 10 ng/ml of IL-18, 2 ng/ml of IL-12 in 96-well plates at 37° C. under 5% $CO_2$ overnight. The cells were spun down and supernatant was collected for IFN-gamma ELISA analysis using BD OptEIA human IFN-gamma ELISA set (Cat#555142) (BD Biosciences). Absorbance was read using Spectromax microplate reader and the data was analyzed using PRISM (GraphPad Software). Results are shown in Table 9.

TABLE 9

| Antibody | human WB-assay COPD patients IC90 [pM] | human WB-assay healthy non-smokers IC90 [pM] |
|---|---|---|
| Mab1G12 | 42.1 | 12.2 |
| Mab2D11 | — | 19.2 |
| 'MS' | — | 33.0 |
| 'Reg' | — | 21.6 |

Example 13

Binding of Mab1G12 and Mab2D11 to IL-18R Variants

For the investigation of the antibody binding site IL-18Rα was cloned and expressed as Fc-fusion protein (human IgG1 Hinge until $CH_3$). IL-18Rα is composed of 3 Ig-like domains D1, D2, D3 (SWISS Prot Acc No. Q13478). Several variants and mutants were generated and residual binding of the ABs 1G12 and 2D11 was tested. Mutations were introduced by exchanging human IL-18Rα-sequences with corresponding mouse IL-18Rα sequences. Deletions were performed by separate cloning and expression of domains as human Fc-fusion proteins. Further cynomolgus IL-18Rα was cloned as human Fc-fusion protein. Results are shown in table 8. Binding of antibodies to different IL18Rα-variants was measured by Surface Plasmon Resonance (SPR) using a BIAcore® 3000 instrument (GE Healthcare) at 25° C. Amine coupling of around 500 resonance units (RU) of a capturing system (capturing mAB specific for human IgG, Jackson Immunoresearch/109-005-098) was performed on a CM3 chip at pH 5.0 using an amine coupling kit supplied by the GE Healthcare. For analysis different human Fc-tagged IL18Rα-variants were captured by injecting a 10 µg/ml solution for 2 min at a flow of 10 µl/min. Excess binding sites were blocked by injecting a human Fc mixture at a concentration of 1.25 µM (Biodesign, 50175). Then the antibody to be tested was injected at a concentration of 0.2 µg/ml for 3 min at a flow of 10 µl/min. The dissociation phase was monitored for up to 5 min and triggered by switching from the sample solution to running buffer. If the natural ligands IL-18 and IL-18Rβ were tested a mixture of both proteins at a concentration of 100 nM was injected as described above for an antibody. The surface was regenerated by 1 min washing with a 100 mM phosphoric acid solution followed by 1 min washing with 5 mM NaOH at a flow rate of 10 µL/min. Bulk refractive index differences were corrected by subtracting the response obtained from a blank-coupled surface. Blank injections are also substracted (=double referencing). IL-18Rα variants being bound by antibodies comparable to the IL-18Rα wildtype do not influence the binding of such antibodies and it is therefore concluded that inserted/changed mutations do not contribute to the binding (marked with + in Table 7). Influenced binding denotes if the binding signal is reduced by 20-50% compared to the binding signal seen by the wildtype. Weak binding denotes a clear binding 10% above the signal but less than 50% described for the wildtype receptor (marked as 0). If no binding is detected it is marked with – in table 10.

Mutations and Variants of shIL-18Rα:Fc

1. WT wild type shIL-18Rα:Fc
2. cynocynomolgus IL-18Rα:Fc
3. D3 Deletion D1/D2; residual D3
4. D1-1 D1-mutation SRIAL to PRVTF
5. D1-2 D1-mutation MKNYTQK to VGNDRRN
6. D2-1 D2-mutation QTLVNSTS to EELIQDTW
7. D2-2 D2-mutation NPTIKKN to TPRILKD
8. D2-3 D2-mutation HFLHHNGKLF to FSVHHNGTRY

TABLE 10

|  | 1G12 | 2D11 | Reg | MS | IL-18/ IL-18Rβ (control) |
|---|---|---|---|---|---|
| 1. WT | + | + | + | + | + |
| 2. cyno | + | + | + | + | + |
| 3. D3 | – | – | + | + | – |
| 4. D1-1 | + | + | + | + | + |
| 5. D1-2 | + | + | + | + | + |
| 6. D2-1 | + | + | n.d. | n.d, | + |

TABLE 10-continued

|   | 1G12 | 2D11 | Reg | MS | IL-18/ IL-18Rβ (control) |
|---|---|---|---|---|---|
| 7. D2-2 | + | + | n.d. | n.d, | + |
| 8. D2-3 | + | + | n.d. | n.d, | + |

Legend:
+ = binding
+/− = decreased binding
0 = weak binding
− = no detectable binding

Example 14

Binding Assay for IL-18R Peptides

Binding of antibodies to peptides described as SEQ ID NO:5 and 6 in US20080063644 was investigated. These peptides were N-terminally biotinylated and probed for binding by SPR. Binding of antibodies to these peptides was measured by Surface Plasmon Resonance (SPR) using a BIAcore® 3000 instrument (GE Healthcare) at 25° C. and HBS-P+ as running and diluation buffer. Biotinylated peptides were immobilized on a SA chip by injecting several pulses (60 sec) of a 10 nM peptide solution yielding a response of 40 RU. The reference surface as well as the coated surfaces were deactivated by injecting free Biotin at a concentration of 1 µM. For analysis the antibody to be tested was injected at a concentration of 100 nM for 3 min at a flow of 10 µl/min. The dissociation phase was monitored for up to 2.5 min and triggered by switching from the sample solution to running buffer. Bulk refractive index differences were corrected by subtracting the response obtained from a blank-coupled surface. Blank injections are also substracted (=double referencing). For antibody Mab1G12 no binding could be detected to these peptides.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An isolated antibody that binds to human IL-18R1 comprising as heavy chain variable region CDRs a CDRH1 region of SEQ ID NO:2 or SEQ ID NO:10, a CDRH2 region of SEQ ID NO:3 and a CDRH3 region of SEQ ID NO:4, and as light chain variable region CDRs a CDRL1 region of SEQ ID NO:6, a CDRL2 region of SEQ ID NO:7 and a CDRL3 region of SEQ ID NO:8 or a humanized version thereof.

2. The antibody of claim 1 wherein said antibody comprises:
   a. a variable heavy chain region comprising SEQ ID NO:1 and a variable light chain region comprising SEQ ID NO:5; or
   b. a heavy chain variable region comprising SEQ ID NO:9 and a variable light chain region comprising SEQ ID NO:11,
   c. a humanized version of (a) or (b).

3. The antibody of claim 1 wherein said antibody binds to human IL-18R1 with a binding affinity of $10^{-8}$ M or less.

4. The antibody of claim 1 wherein the antibody is a human antibody.

5. The antibody of claim 4 wherein the antibody is either IgG1 or IgG4.

6. An isolated antibody that binds to human IL-18R1 wherein said antibody binds to the same human IL-18R1 epitope to which a monoclonal antibody comprising a variable heavy chain region comprising SEQ ID NO:1 and a variable light chain region comprising SEQ ID NO:5 binds.

7. The antibody of claim 1 wherein said antibody binds to human IL-18R1 with a binding affinity of $10^{-8}$ M or less.

8. The antibody according to claim 6, wherein the isolated antibody has variable heavy chain region and variable light chain region CDRs selected from:
   a) as heavy chain variable region CDRs a CDRH1 region of SEQ ID NO:30, a CDRH2 region of SEQ ID NO:31 and a CDRH3 region of SEQ ID NO:32, and as light chain variable region CDRs a CDRL1 region of SEQ ID NO:34, a CDRL2 region of SEQ ID NO:35 and a CDRL3 region of SEQ ID NO:36;
   b) as heavy chain variable region CDRs a CDRH1 region of SEQ ID NO: 38, a CDRH2 region of SEQ ID NO:39 and a CDRH3 region of SEQ ID NO:40, and as light chain variable region CDRs a CDRL1 region of SEQ ID NO:42, a CDRL2 region of SEQ ID NO:43 and a CDRL3 region of SEQ ID NO:44;
   c) as heavy chain variable region CDRs a CDRH1 region of SEQ ID NO:46, a CDRH2 region of SEQ ID NO:47 and a CDRH3 region of SEQ ID NO:48, and as light chain variable region CDRs a CDRL1 region of SEQ ID NO:50, a CDRL2 region of SEQ ID NO:51 and a CDRL3 region of SEQ ID NO:52;
   d) as heavy chain variable region CDRs a CDRH1 region of SEQ ID NO:54, a CDRH2 region of SEQ ID NO:55 and a CDRH3 region of SEQ ID NO:56, and as light chain variable region CDRs a CDRL1 region of SEQ ID NO:58, a CDRL2 region of SEQ ID NO:59 and a CDRL3 region of SEQ ID NO:60; or
   e) as heavy chain variable region CDRs a CDRH1 region of SEQ ID NO:62, a CDRH2 region of SEQ ID NO:63 and a CDRH3 region of SEQ ID NO:64, and as light chain variable region CDRs a CDRL1 region of SEQ ID NO:66, a CDRL2 region of SEQ ID NO:67 and a CDRL3 region of SEQ ID NO:68.

9. The antibody according to claim 6, wherein the isolated antibody has a variable heavy chain region and a variable light chain region selected from:
   a) as heavy chain variable region SEQ ID NO:29 and as variable light chain region SEQ ID NO:33;
   b) as heavy chain variable region SEQ ID NO:37 and as variable light chain region SEQ ID NO:41;
   c) as heavy chain variable region SEQ ID NO:45 and as variable light chain region SEQ ID NO:49;
   d) as heavy chain variable region SEQ ID NO:53 and as variable light chain region SEQ ID NO:57; or
   e) as heavy chain variable region SEQ ID NO:61 and as variable light chain region SEQ ID NO:65.

10. The antibody according to claim 5, wherein the antibody is human IgG1 isotype comprising mutations L234A and L235A.

11. The antibody according to claim 5, wherein the antibody is human IgG4 isotype comprising a S228P mutation.

12. The antibody according to claim 11 further comprising mutation L235E.

13. A pharmaceutical formulation comprising the antibody according to claim 1 and a pharmaceutically acceptable carrier.

14. The antibody according to claim 1, wherein the antibody is partially fucosylated.

15. The antibody according to claim 1, wherein the antibody is afucosylated.

16. A pharmaceutical formulation comprising the antibody according to claim 1 and a pharmaceutically acceptable carrier.

17. The antibody according to claim 1 wherein said antibody blocks the interaction between IL-18 and IL-18R1.

18. The antibody according to claim 1 wherein said antibody blocks formation of an IL-18R1 and IL18RAP complex.

19. The antibody according to claim 1 wherein said antibody inhibits Il-18 receptor complex mediated signaling.

20. The antibody according to claim 1 wherein said antibody blocks NFkappaB pathway activation.

21. An isolated anti-IL-18R1 antibody wherein the antibody comprises complementarity-determining regions (CDRs) (a)-(f):
   (a) a CDR-L1 sequence comprising amino acids XASKSVSTSGDSYMH (SEQ ID NO:69), where X is either R or Q;
   (b) a CDR-L2 sequence comprising amino acids LASNLES (SEQ ID NO:7);
   (c) a CDR-L3 sequence comprising amino acids QQSRELPLS (SEQ ID NO:8);
   (d) a CDR-H1 sequence comprising amino acids XYTFT (SEQ ID NO:70), where X is either D or G;
   (e) a CDR-H2 sequence comprising amino acids TIDPSDSYTYYX$_1$QKX$_2$X$_3$G (SEQ ID NO: 71), wherein X$_1$ is N or A, X$_2$ is F or A, and X$_3$ is K or Q; and
   (f) a CDR-H3 sequence comprising amino acids SGDYDADRYFDV (SEQ ID NO:4).

22. The antibody of claim 21, wherein the antibody is humanized.

* * * * *

SEQUENCE LISTING

```
<160> NUMBER OF SEQ ID NOS: 72

<210> SEQ ID NO 1
<211> LENGTH: 121
<212> TYPE: PRT
<213> ORGANISM: Mus musculus

<400> SEQUENCE: 1

Gln Val Gln Leu Gln Gln Pro Gly Ala Glu Leu Val Lys Pro Gly Ala
1               5                   10                  15

Ser Val Arg Met Ser Cys Lys Thr Ser Asp Tyr Thr Phe Thr Ser Asn
            20                  25                  30

Trp Met His Trp Val Lys Gln Arg Pro Gly Gln Gly Leu Glu Trp Ile
        35                  40                  45

Gly Thr Ile Asp Pro Ser Asp Ser Tyr Thr Tyr Tyr Asn Gln Lys Phe
    50                  55                  60

Lys Gly Arg Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Thr Ser Gly Asp Tyr Asp Ala Asp Arg Tyr Phe Asp Val Trp Gly
            100                 105                 110

Ala Gly Thr Thr Val Thr Val Ser Ser
        115                 120

<210> SEQ ID NO 2
<211> LENGTH: 5
<212> TYPE: PRT
<213> ORGANISM: Mus musculus

<400> SEQUENCE: 2

Asp Tyr Thr Phe Thr
1               5

<210> SEQ ID NO 3
<211> LENGTH: 17
<212> TYPE: PRT
<213> ORGANISM: Mus musculus
```

```
<400> SEQUENCE: 3

Thr Ile Asp Pro Ser Asp Ser Tyr Thr Tyr Tyr Asn Gln Lys Phe Lys
1               5                   10                  15

Gly

<210> SEQ ID NO 4
<211> LENGTH: 12
<212> TYPE: PRT
<213> ORGANISM: Mus musculus

<400> SEQUENCE: 4

Ser Gly Asp Tyr Asp Ala Asp Arg Tyr Phe Asp Val
1               5                   10

<210> SEQ ID NO 5
<211> LENGTH: 111
<212> TYPE: PRT
<213> ORGANISM: Mus musculus

<400> SEQUENCE: 5

Asp Ile Val Leu Thr Gln Ser Pro Ala Ser Leu Gly Val Ser Leu Gly
1               5                   10                  15

Gln Arg Ala Thr Ile Ser Cys Arg Ala Ser Lys Ser Val Ser Thr Ser
            20                  25                  30

Gly Asp Ser Tyr Met His Trp Tyr Gln Gln Lys Pro Gly Gln Ser Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95

Glu Leu Pro Leu Ser Phe Gly Ala Gly Thr Lys Leu Glu Leu Lys
            100                 105                 110

<210> SEQ ID NO 6
<211> LENGTH: 15
<212> TYPE: PRT
<213> ORGANISM: Mus musculus

<400> SEQUENCE: 6

Arg Ala Ser Lys Ser Val Ser Thr Ser Gly Asp Ser Tyr Met His
1               5                   10                  15

<210> SEQ ID NO 7
<211> LENGTH: 7
<212> TYPE: PRT
<213> ORGANISM: Mus musculus

<400> SEQUENCE: 7

Leu Ala Ser Asn Leu Glu Ser
1               5

<210> SEQ ID NO 8
<211> LENGTH: 9
<212> TYPE: PRT
<213> ORGANISM: Mus musculus

<400> SEQUENCE: 8

Gln Gln Ser Arg Glu Leu Pro Leu Ser
1               5
```

```
<210> SEQ ID NO 9
<211> LENGTH: 121
<212> TYPE: PRT
<213> ORGANISM: Mus musculus

<400> SEQUENCE: 9

Gln Val Gln Leu Gln Gln Pro Gly Ala Glu Leu Val Lys Pro Gly Ala
1               5                   10                  15

Ser Val Lys Met Ser Cys Lys Ala Ser Asp Tyr Thr Phe Thr Ser Asn
            20                  25                  30

Trp Met His Trp Val Lys Gln Arg Pro Gly Gln Gly Leu Glu Trp Ile
        35                  40                  45

Gly Thr Ile Asp Pro Ser Asp Ser Tyr Thr Tyr Tyr Asn Gln Lys Phe
    50                  55                  60

Lys Gly Lys Ala Thr Leu Thr Val Asp Thr Ser Ser Thr Ala Tyr
65                  70                  75                  80

Met His Leu Ser Ser Leu Thr Ser Glu Asp Ser Ala Val Tyr Tyr Cys
                85                  90                  95

Thr Thr Ser Gly Asp Tyr Asp Ala Asp Arg Tyr Phe Asp Val Trp Gly
            100                 105                 110

Ala Gly Thr Thr Val Thr Val Ser Ser
        115                 120

<210> SEQ ID NO 10
<211> LENGTH: 10
<212> TYPE: PRT
<213> ORGANISM: Mus musculus

<400> SEQUENCE: 10

Asp Tyr Thr Phe Thr Ser Asn Trp Met His
1               5                   10

<210> SEQ ID NO 11
<211> LENGTH: 111
<212> TYPE: PRT
<213> ORGANISM: Mus musculus

<400> SEQUENCE: 11

Asp Ile Val Leu Thr Gln Ser Pro Ala Ser Leu Gly Val Ser Leu Gly
1               5                   10                  15

Gln Arg Ala Thr Ile Ser Cys Arg Ala Ser Lys Ser Val Ser Thr Ser
            20                  25                  30

Gly Asp Ser Tyr Met His Trp Tyr Gln Gln Lys Pro Gly Gln Ser Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Arg
                85                  90                  95

Glu Leu Pro Leu Ser Phe Gly Ala Gly Thr Lys Leu Glu Leu Lys
            100                 105                 110

<210> SEQ ID NO 12
<211> LENGTH: 107
<212> TYPE: PRT
<213> ORGANISM: homo sapiens
```

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 105
<212> TYPE: PRT
<213> ORGANISM: homo sapiens

<400> SEQUENCE: 13

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65              70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 14
<211> LENGTH: 330
<212> TYPE: PRT
<213> ORGANISM: homo sapiens

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys

```
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 15
<211> LENGTH: 330
<212> TYPE: PRT
<213> ORGANISM: homo sapiens

<400> SEQUENCE: 15

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 17
<211> LENGTH: 327
<212> TYPE: PRT
<213> ORGANISM: homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys

```
                225                 230                 235                 240
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 18
<211> LENGTH: 327
<212> TYPE: PRT
<213> ORGANISM: homo sapiens

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

Thr Thr Pro Pro Val Leu Asp Ser Asp Gly Ser Phe Phe Leu Tyr Ser
              275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 19
<211> LENGTH: 5
<212> TYPE: PRT
<213> ORGANISM: Homo sapiens

<400> SEQUENCE: 19

Ser Arg Ile Ala Leu
1               5

<210> SEQ ID NO 20
<211> LENGTH: 5
<212> TYPE: PRT
<213> ORGANISM: Homo sapiens

<400> SEQUENCE: 20

Pro Arg Val Thr Phe
1               5

<210> SEQ ID NO 21
<211> LENGTH: 7
<212> TYPE: PRT
<213> ORGANISM: Homo sapiens

<400> SEQUENCE: 21

Met Lys Asn Tyr Thr Gln Lys
1               5

<210> SEQ ID NO 22
<211> LENGTH: 7
<212> TYPE: PRT
<213> ORGANISM: Homo sapiens

<400> SEQUENCE: 22

Val Gly Asn Asp Arg Arg Asn
1               5

<210> SEQ ID NO 23
<211> LENGTH: 8
<212> TYPE: PRT
<213> ORGANISM: Homo sapiens

<400> SEQUENCE: 23

Gln Thr Leu Val Asn Ser Thr Ser
1               5

<210> SEQ ID NO 24
<211> LENGTH: 8
<212> TYPE: PRT
<213> ORGANISM: Homo sapiens

<400> SEQUENCE: 24

Glu Glu Leu Ile Gln Asp Thr Trp
1               5

<210> SEQ ID NO 25
<211> LENGTH: 7
<212> TYPE: PRT
<213> ORGANISM: Homo sapiens

<400> SEQUENCE: 25

Asn Pro Thr Ile Lys Lys Asn
1               5

<210> SEQ ID NO 26
<211> LENGTH: 7
<212> TYPE: PRT
<213> ORGANISM: Homo sapiens

<400> SEQUENCE: 26

Thr Pro Arg Ile Leu Lys Asp
1               5

<210> SEQ ID NO 27
<211> LENGTH: 10
<212> TYPE: PRT
<213> ORGANISM: Homo sapiens

<400> SEQUENCE: 27

His Phe Leu His His Asn Gly Lys Leu Phe
1               5                   10

<210> SEQ ID NO 28
<211> LENGTH: 10
<212> TYPE: PRT
<213> ORGANISM: Homo sapiens

<400> SEQUENCE: 28

Phe Ser Val His His Asn Gly Thr Arg Tyr
1               5                   10

<210> SEQ ID NO 29
<211> LENGTH: 121
<212> TYPE: PRT
<213> ORGANISM: Artificial
<220> FEATURE:
<223> OTHER INFORMATION: heavy chain variable region (VH) of humanized
      Mab1G12-9.6

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Ser Asn
            20                  25                  30

Trp Met His Trp Val Arg Gln Ala Pro Gly Gln Gly Leu Glu Trp Met
        35                  40                  45

Gly Thr Ile Asp Pro Ser Asp Ser Tyr Thr Tyr Tyr Asn Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Gly Asp Tyr Asp Ala Asp Arg Tyr Phe Asp Val Trp Gly
            100                 105                 110

Gln Gly Thr Thr Val Thr Val Ser Ser
        115                 120

```
<210> SEQ ID NO 30
<211> LENGTH: 5
<212> TYPE: PRT
<213> ORGANISM: Artificial
<220> FEATURE:
<223> OTHER INFORMATION: heavy chain CDRH1 humanized Mab1G12-9.6

<400> SEQUENCE: 30

Asp Tyr Thr Phe Thr
1               5

<210> SEQ ID NO 31
<211> LENGTH: 17
<212> TYPE: PRT
<213> ORGANISM: Artificial
<220> FEATURE:
<223> OTHER INFORMATION: heavy chain CDRH2 humanized Mab1G12-9.6

<400> SEQUENCE: 31

Thr Ile Asp Pro Ser Asp Ser Tyr Thr Tyr Tyr Asn Gln Lys Phe Gln
1               5                   10                  15

Gly

<210> SEQ ID NO 32
<211> LENGTH: 12
<212> TYPE: PRT
<213> ORGANISM: Artificial
<220> FEATURE:
<223> OTHER INFORMATION: heavy chain CDRH3 humanized Mab1G12-9.6

<400> SEQUENCE: 32

Ser Gly Asp Tyr Asp Ala Asp Arg Tyr Phe Asp Val
1               5                   10

<210> SEQ ID NO 33
<211> LENGTH: 111
<212> TYPE: PRT
<213> ORGANISM: Artificial
<220> FEATURE:
<223> OTHER INFORMATION: light chain variable region (VL) of humanized
      Mab1G12-9.6

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Val Ser Thr Ser
                20                  25                  30

Gly Asp Ser Tyr Met His Trp Tyr Gln Gln Lys Pro Gly Gln Ala Pro
            35                  40                  45

Arg Leu Leu Ile Tyr Leu Ala Ser Asn Leu Glu Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Arg
                85                  90                  95

Glu Leu Pro Leu Ser Phe Gly Gln Gly Thr Lys Leu Glu Ile Lys
            100                 105                 110

<210> SEQ ID NO 34
<211> LENGTH: 15
<212> TYPE: PRT
<213> ORGANISM: Artificial
<220> FEATURE:
<223> OTHER INFORMATION: light chain CDRL1 humanized Mab1G12-9.6
```

<400> SEQUENCE: 34

Arg Ala Ser Lys Ser Val Ser Thr Ser Gly Asp Ser Tyr Met His
1               5                   10                  15

<210> SEQ ID NO 35
<211> LENGTH: 7
<212> TYPE: PRT
<213> ORGANISM: Artificial
<220> FEATURE:
<223> OTHER INFORMATION: light chain CDRL2 humanized Mab1G12-9.6

<400> SEQUENCE: 35

Leu Ala Ser Asn Leu Glu Thr
1               5

<210> SEQ ID NO 36
<211> LENGTH: 9
<212> TYPE: PRT
<213> ORGANISM: Artificial
<220> FEATURE:
<223> OTHER INFORMATION: light chain CDRL3 humanized Mab1G12-9.6

<400> SEQUENCE: 36

Gln Gln Ser Arg Glu Leu Pro Leu Ser
1               5

<210> SEQ ID NO 37
<211> LENGTH: 121
<212> TYPE: PRT
<213> ORGANISM: Artificial
<220> FEATURE:
<223> OTHER INFORMATION: heavy chain variable region (VH) of humanized
      Mab1G12-10.5

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Ser Asn
                20                  25                  30

Trp Met His Trp Val Arg Gln Ala Pro Gly Gln Gly Leu Glu Trp Met
            35                  40                  45

Gly Thr Ile Asp Pro Ser Asp Ser Tyr Thr Tyr Tyr Asn Gln Lys Phe
        50                  55                  60

Gln Gly Arg Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Gly Asp Tyr Asp Ala Asp Arg Tyr Phe Asp Val Trp Gly
                100                 105                 110

Gln Gly Thr Thr Val Thr Val Ser Ser
            115                 120

<210> SEQ ID NO 38
<211> LENGTH: 5
<212> TYPE: PRT
<213> ORGANISM: Artificial
<220> FEATURE:
<223> OTHER INFORMATION: heavy chain CDRH1 humanized Mab1G12-10.5

<400> SEQUENCE: 38

Asp Tyr Thr Phe Thr
1               5

<210> SEQ ID NO 39
<211> LENGTH: 17
<212> TYPE: PRT
<213> ORGANISM: Artificial
<220> FEATURE:
<223> OTHER INFORMATION: heavy chain CDRH2 humanized Mab1G12-10.5

<400> SEQUENCE: 39

Thr Ile Asp Pro Ser Asp Ser Tyr Thr Tyr Tyr Asn Gln Lys Phe Gln
1               5                   10                  15
Gly

<210> SEQ ID NO 40
<211> LENGTH: 12
<212> TYPE: PRT
<213> ORGANISM: Artificial
<220> FEATURE:
<223> OTHER INFORMATION: heavy chain CDRH3 humanized Mab1G12-10.5

<400> SEQUENCE: 40

Ser Gly Asp Tyr Asp Ala Asp Arg Tyr Phe Asp Val
1               5                   10

<210> SEQ ID NO 41
<211> LENGTH: 111
<212> TYPE: PRT
<213> ORGANISM: Artificial
<220> FEATURE:
<223> OTHER INFORMATION: light chain variable region (VL) of humanized
      Mab1G12-10.5

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Lys Ser Val Ser Thr Ser
            20                  25                  30

Gly Asp Ser Tyr Met His Trp Tyr Gln Gln Lys Pro Gly Lys Ala Pro
        35                  40                  45

Lys Leu Leu Ile Tyr Leu Ala Ser Asn Leu Glu Thr Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Arg
                85                  90                  95

Glu Leu Pro Leu Ser Phe Gly Gln Gly Thr Lys Leu Glu Ile Lys
            100                 105                 110

<210> SEQ ID NO 42
<211> LENGTH: 15
<212> TYPE: PRT
<213> ORGANISM: Artificial
<220> FEATURE:
<223> OTHER INFORMATION: light chain CDRL1 humanized Mab1G12-10.5

<400> SEQUENCE: 42

Gln Ala Ser Lys Ser Val Ser Thr Ser Gly Asp Ser Tyr Met His
1               5                   10                  15

<210> SEQ ID NO 43
<211> LENGTH: 7
<212> TYPE: PRT
<213> ORGANISM: Artificial

```
<220> FEATURE:
<223> OTHER INFORMATION: light chain CDRL2 humanized Mab1G12-10.5

<400> SEQUENCE: 43

Leu Ala Ser Asn Leu Glu Thr
1               5

<210> SEQ ID NO 44
<211> LENGTH: 9
<212> TYPE: PRT
<213> ORGANISM: Artificial
<220> FEATURE:
<223> OTHER INFORMATION: light chain CDRL3 humanized Mab1G12-10.5

<400> SEQUENCE: 44

Gln Gln Ser Arg Glu Leu Pro Leu Ser
1               5

<210> SEQ ID NO 45
<211> LENGTH: 121
<212> TYPE: PRT
<213> ORGANISM: Artificial
<220> FEATURE:
<223> OTHER INFORMATION: heavy chain variable region (VH) of humanized
      Mab1G12-10.6

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Ser Asn
            20                  25                  30

Trp Met His Trp Val Arg Gln Ala Pro Gly Gln Gly Leu Glu Trp Met
        35                  40                  45

Gly Thr Ile Asp Pro Ser Asp Ser Tyr Thr Tyr Tyr Asn Gln Lys Phe
    50                  55                  60

Gln Gly Arg Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Thr Ser Gly Asp Tyr Asp Ala Asp Arg Tyr Phe Asp Val Trp Gly
            100                 105                 110

Gln Gly Thr Val Thr Val Ser Ser
        115                 120

<210> SEQ ID NO 46
<211> LENGTH: 5
<212> TYPE: PRT
<213> ORGANISM: Artificial
<220> FEATURE:
<223> OTHER INFORMATION: heavy chain CDRH1 humanized Mab1G12-10.6

<400> SEQUENCE: 46

Asp Tyr Thr Phe Thr
1               5

<210> SEQ ID NO 47
<211> LENGTH: 17
<212> TYPE: PRT
<213> ORGANISM: Artificial
<220> FEATURE:
<223> OTHER INFORMATION: heavy chain CDRH2 humanized Mab1G12-10.6

<400> SEQUENCE: 47
```

```
Thr Ile Asp Pro Ser Asp Ser Tyr Thr Tyr Tyr Asn Gln Lys Phe Gln
1               5                   10                  15

Gly
```

<210> SEQ ID NO 48
<211> LENGTH: 12
<212> TYPE: PRT
<213> ORGANISM: Artificial
<220> FEATURE:
<223> OTHER INFORMATION: heavy chain CDRH3 humanized Mab1G12-10.6

<400> SEQUENCE: 48

```
Ser Gly Asp Tyr Asp Ala Asp Arg Tyr Phe Asp Val
1               5                   10
```

<210> SEQ ID NO 49
<211> LENGTH: 111
<212> TYPE: PRT
<213> ORGANISM: Artificial
<220> FEATURE:
<223> OTHER INFORMATION: light chain variable region (VL) of humanized
      Mab1G12-10.6

<400> SEQUENCE: 49

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Asp Ser Tyr Met His Trp Tyr Gln Gln Lys Pro Gly Gln Ala Pro
        35                  40                  45

Arg Leu Leu Ile Tyr Leu Ala Ser Asn Leu Glu Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Arg
                85                  90                  95

Glu Leu Pro Leu Ser Phe Gly Gln Gly Thr Lys Leu Glu Ile Lys
            100                 105                 110
```

<210> SEQ ID NO 50
<211> LENGTH: 15
<212> TYPE: PRT
<213> ORGANISM: Artificial
<220> FEATURE:
<223> OTHER INFORMATION: light chain CDRL1 humanized Mab1G12-10.6

<400> SEQUENCE: 50

```
Arg Ala Ser Lys Ser Val Ser Thr Ser Gly Asp Ser Tyr Met His
1               5                   10                  15
```

<210> SEQ ID NO 51
<211> LENGTH: 7
<212> TYPE: PRT
<213> ORGANISM: Artificial
<220> FEATURE:
<223> OTHER INFORMATION: light chain CDRL2 humanized Mab1G12-10.6

<400> SEQUENCE: 51

```
Leu Ala Ser Asn Leu Glu Thr
1               5
```

<210> SEQ ID NO 52
<211> LENGTH: 9

```
<212> TYPE: PRT
<213> ORGANISM: Artificial
<220> FEATURE:
<223> OTHER INFORMATION: light chain CDRL3 humanized Mab1G12-10.6

<400> SEQUENCE: 52

Gln Gln Ser Arg Glu Leu Pro Leu Ser
1               5

<210> SEQ ID NO 53
<211> LENGTH: 121
<212> TYPE: PRT
<213> ORGANISM: Artificial
<220> FEATURE:
<223> OTHER INFORMATION: heavy chain variable region (VH) of humanized
      Mab1G12-11.6

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Arg Gln Ala Pro Gly Gln Gly Leu Glu Trp Met
        35                  40                  45

Gly Thr Ile Asp Pro Ser Asp Ser Tyr Thr Tyr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Thr Ser Gly Asp Tyr Asp Ala Asp Arg Tyr Phe Asp Val Trp Gly
            100                 105                 110

Gln Gly Thr Thr Val Thr Val Ser Ser
        115                 120

<210> SEQ ID NO 54
<211> LENGTH: 5
<212> TYPE: PRT
<213> ORGANISM: Artificial
<220> FEATURE:
<223> OTHER INFORMATION: heavy chain CDRH1 humanized Mab1G12-11.6

<400> SEQUENCE: 54

Gly Tyr Thr Phe Thr
1               5

<210> SEQ ID NO 55
<211> LENGTH: 17
<212> TYPE: PRT
<213> ORGANISM: Artificial
<220> FEATURE:
<223> OTHER INFORMATION: heavy chain CDRH2 humanized Mab1G12-11.6

<400> SEQUENCE: 55

Thr Ile Asp Pro Ser Asp Ser Tyr Thr Tyr Tyr Ala Gln Lys Phe Gln
1               5                   10                  15

Gly

<210> SEQ ID NO 56
<211> LENGTH: 12
<212> TYPE: PRT
<213> ORGANISM: Artificial
<220> FEATURE:
```

-continued

<223> OTHER INFORMATION: heavy chain CDRH3 humanized Mab1G12-11.6

<400> SEQUENCE: 56

Ser Gly Asp Tyr Asp Ala Asp Arg Tyr Phe Asp Val
1               5                   10

<210> SEQ ID NO 57
<211> LENGTH: 111
<212> TYPE: PRT
<213> ORGANISM: Artificial
<220> FEATURE:
<223> OTHER INFORMATION: light chain variable region (VL) of humanized
      Mab1G12-11.6

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Asp Ser Tyr Met His Trp Tyr Gln Gln Lys Pro Gly Gln Ala Pro
        35                  40                  45

Arg Leu Leu Ile Tyr Leu Ala Ser Asn Leu Glu Thr Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Arg
                85                  90                  95

Glu Leu Pro Leu Ser Phe Gly Gln Gly Thr Lys Leu Glu Ile Lys
            100                 105                 110

<210> SEQ ID NO 58
<211> LENGTH: 15
<212> TYPE: PRT
<213> ORGANISM: Artificial
<220> FEATURE:
<223> OTHER INFORMATION: light chain CDRL1 humanized Mab1G12-11.6

<400> SEQUENCE: 58

Arg Ala Ser Lys Ser Val Ser Thr Ser Gly Asp Ser Tyr Met His
1               5                   10                  15

<210> SEQ ID NO 59
<211> LENGTH: 7
<212> TYPE: PRT
<213> ORGANISM: Artificial
<220> FEATURE:
<223> OTHER INFORMATION: light chain CDRL2 humanized Mab1G12-11.6

<400> SEQUENCE: 59

Leu Ala Ser Asn Leu Glu Thr
1               5

<210> SEQ ID NO 60
<211> LENGTH: 9
<212> TYPE: PRT
<213> ORGANISM: Artificial
<220> FEATURE:
<223> OTHER INFORMATION: light chain CDRL3 humanized Mab1G12-11.6

<400> SEQUENCE: 60

Gln Gln Ser Arg Glu Leu Pro Leu Ser
1               5

<210> SEQ ID NO 61
<211> LENGTH: 121
<212> TYPE: PRT
<213> ORGANISM: Artificial
<220> FEATURE:
<223> OTHER INFORMATION: heavy chain variable region (VH) of humanized
      Mab1G12-12.6

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Trp Met His Trp Val Arg Gln Ala Pro Gly Gln Gly Leu Glu Trp Met
        35                  40                  45

Gly Thr Ile Asp Pro Ser Asp Ser Tyr Thr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Thr Ser Gly Asp Tyr Asp Ala Asp Arg Tyr Phe Asp Val Trp Gly
            100                 105                 110

Gln Gly Thr Thr Val Thr Val Ser Ser
        115                 120

<210> SEQ ID NO 62
<211> LENGTH: 5
<212> TYPE: PRT
<213> ORGANISM: Artificial
<220> FEATURE:
<223> OTHER INFORMATION: heavy chain CDRH1 humanized Mab1G12-12.6

<400> SEQUENCE: 62

Gly Tyr Thr Phe Thr
1               5

<210> SEQ ID NO 63
<211> LENGTH: 17
<212> TYPE: PRT
<213> ORGANISM: Artificial
<220> FEATURE:
<223> OTHER INFORMATION: heavy chain CDRH2 humanized Mab1G12-12.6

<400> SEQUENCE: 63

Thr Ile Asp Pro Ser Asp Ser Tyr Thr Tyr Ala Gln Lys Leu Gln
1               5                   10                  15

Gly

<210> SEQ ID NO 64
<211> LENGTH: 12
<212> TYPE: PRT
<213> ORGANISM: Artificial
<220> FEATURE:
<223> OTHER INFORMATION: heavy chain CDRH3 humanized Mab1G12-12.6

<400> SEQUENCE: 64

Ser Gly Asp Tyr Asp Ala Asp Arg Tyr Phe Asp Val
1               5                   10

<210> SEQ ID NO 65
<211> LENGTH: 111
<212> TYPE: PRT

<213> ORGANISM: Artificial
<220> FEATURE:
<223> OTHER INFORMATION: light chain variable region (VL) of humanized Mab1G12-12.6

<400> SEQUENCE: 65

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Lys Ser Val Ser Thr Ser
            20                  25                  30
Gly Asp Ser Tyr Met His Trp Tyr Gln Gln Lys Pro Gly Gln Ala Pro
        35                  40                  45
Arg Leu Leu Ile Tyr Leu Ala Ser Asn Leu Glu Thr Gly Ile Pro Asp
    50                  55                  60
Arg Phe Ser Gly Ser Gly Ser Gly Thr Asp Phe Thr Leu Thr Ile Ser
65                  70                  75                  80
Arg Leu Glu Pro Glu Asp Phe Ala Val Tyr Tyr Cys Gln Gln Ser Arg
                85                  90                  95
Glu Leu Pro Leu Ser Phe Gly Gln Gly Thr Lys Leu Glu Ile Lys
            100                 105                 110
```

<210> SEQ ID NO 66
<211> LENGTH: 15
<212> TYPE: PRT
<213> ORGANISM: Artificial
<220> FEATURE:
<223> OTHER INFORMATION: light chain CDRL1 humanized Mab1G12-12.6

<400> SEQUENCE: 66

```
Arg Ala Ser Lys Ser Val Ser Thr Ser Gly Asp Ser Tyr Met His
1               5                   10                  15
```

<210> SEQ ID NO 67
<211> LENGTH: 7
<212> TYPE: PRT
<213> ORGANISM: Artificial
<220> FEATURE:
<223> OTHER INFORMATION: light chain CDRL2 humanized Mab1G12-12.6

<400> SEQUENCE: 67

```
Leu Ala Ser Asn Leu Glu Thr
1               5
```

<210> SEQ ID NO 68
<211> LENGTH: 9
<212> TYPE: PRT
<213> ORGANISM: Artificial
<220> FEATURE:
<223> OTHER INFORMATION: light chain CDRL3 humanized Mab1G12-12.6

<400> SEQUENCE: 68

```
Gln Gln Ser Arg Glu Leu Pro Leu Ser
1               5
```

<210> SEQ ID NO 69
<211> LENGTH: 15
<212> TYPE: PRT
<213> ORGANISM: Artificial
<220> FEATURE:
<223> OTHER INFORMATION: CDRL1 consensus sequence
<220> FEATURE:
<221> NAME/KEY: MISC_FEATURE
<222> LOCATION: (1)..(1)
<223> OTHER INFORMATION: X is either R or Q

<400> SEQUENCE: 69

Xaa Ala Ser Lys Ser Val Ser Thr Ser Gly Asp Ser Tyr Met His
1               5                   10                  15

<210> SEQ ID NO 70
<211> LENGTH: 5
<212> TYPE: PRT
<213> ORGANISM: Artificial
<220> FEATURE:
<223> OTHER INFORMATION: CDRH1 consensus sequence
<220> FEATURE:
<221> NAME/KEY: MISC_FEATURE
<222> LOCATION: (1)..(1)
<223> OTHER INFORMATION: X is either D or G

<400> SEQUENCE: 70

Xaa Tyr Thr Phe Thr
1               5

<210> SEQ ID NO 71
<211> LENGTH: 17
<212> TYPE: PRT
<213> ORGANISM: Artificial
<220> FEATURE:
<223> OTHER INFORMATION: CDRH2 consensus sequence
<220> FEATURE:
<221> NAME/KEY: MISC_FEATURE
<222> LOCATION: (12)..(16)
<223> OTHER INFORMATION: X1 is N or A,
      X2 is F or A, and
      X3 is K or Q
<220> FEATURE:
<221> NAME/KEY: MISC_FEATURE
<222> LOCATION: (12)..(16)
<223> OTHER INFORMATION: X1 is N or A, X2 is F or A, and  X3 is K or Q

<400> SEQUENCE: 71

Thr Ile Asp Pro Ser Asp Ser Tyr Thr Tyr Tyr Xaa Gln Lys Xaa Xaa
1               5                   10                  15

Gly

<210> SEQ ID NO 72
<211> LENGTH: 541
<212> TYPE: PRT
<213> ORGANISM: Homo sapiens

<400> SEQUENCE: 72

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
                20                  25                  30

Gly Glu Pro Phe Tyr Leu Lys His Cys Ser Cys Ser Leu Ala His Glu
            35                  40                  45

Ile Glu Thr Thr Thr Lys Ser Trp Tyr Lys Ser Ser Gly Ser Gln Glu
        50                  55                  60

His Val Glu Leu Asn Pro Arg Ser Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
                100                 105                 110

Arg Arg Asn Lys His Ser Cys Phe Thr Glu Arg Gln Val Thr Ser Lys
            115                 120                 125

```
Ile Val Glu Val Lys Lys Phe Phe Gln Ile Thr Cys Glu Asn Ser Tyr
130                 135                 140
Tyr Gln Thr Leu Val Asn Ser Thr Ser Leu Tyr Lys Asn Cys Lys Lys
145                 150                 155                 160
Leu Leu Leu Glu Asn Asn Lys Asn Pro Thr Ile Lys Lys Asn Ala Glu
                165                 170                 175
Phe Glu Asp Gln Gly Tyr Tyr Ser Cys Val His Phe Leu His His Asn
            180                 185                 190
Gly Lys Leu Phe Asn Ile Thr Lys Thr Phe Asn Ile Thr Ile Val Glu
        195                 200                 205
Asp Arg Ser Asn Ile Val Pro Val Leu Leu Gly Pro Lys Leu Asn His
210                 215                 220
Val Ala Val Glu Leu Gly Lys Asn Val Arg Leu Asn Cys Ser Ala Leu
225                 230                 235                 240
Leu Asn Glu Glu Asp Val Ile Tyr Trp Met Phe Gly Glu Glu Asn Gly
                245                 250                 255
Ser Asp Pro Asn Ile His Glu Glu Lys Glu Met Arg Ile Met Thr Pro
            260                 265                 270
Glu Gly Lys Trp His Ala Ser Lys Val Leu Arg Ile Glu Asn Ile Gly
        275                 280                 285
Glu Ser Asn Leu Asn Val Leu Tyr Asn Cys Thr Val Ala Ser Thr Gly
290                 295                 300
Gly Thr Asp Thr Lys Ser Phe Ile Leu Val Arg Lys Ala Asp Met Ala
305                 310                 315                 320
Asp Ile Pro Gly His Val Phe Thr Arg Gly Met Ile Ile Ala Val Leu
                325                 330                 335
Ile Leu Val Ala Val Val Cys Leu Val Thr Val Cys Val Ile Tyr Arg
            340                 345                 350
Val Asp Leu Val Leu Phe Tyr Arg His Leu Thr Arg Arg Asp Glu Thr
        355                 360                 365
Leu Thr Asp Gly Lys Thr Tyr Asp Ala Phe Val Ser Tyr Leu Lys Glu
370                 375                 380
Cys Arg Pro Glu Asn Gly Glu Glu His Thr Phe Ala Val Glu Ile Leu
385                 390                 395                 400
Pro Arg Val Leu Glu Lys His Phe Gly Tyr Lys Leu Cys Ile Phe Glu
                405                 410                 415
Arg Asp Val Val Pro Gly Gly Ala Val Val Asp Glu Ile His Ser Leu
            420                 425                 430
Ile Glu Lys Ser Arg Arg Leu Ile Ile Val Leu Ser Lys Ser Tyr Met
        435                 440                 445
Ser Asn Glu Val Arg Tyr Glu Leu Glu Ser Gly Leu His Glu Ala Leu
450                 455                 460
Val Glu Arg Lys Ile Lys Ile Ile Leu Ile Glu Phe Thr Pro Val Thr
465                 470                 475                 480
Asp Phe Thr Phe Leu Pro Gln Ser Leu Lys Leu Leu Lys Ser His Arg
                485                 490                 495
Val Leu Lys Trp Lys Ala Asp Lys Ser Leu Ser Tyr Asn Ser Arg Phe
            500                 505                 510
Trp Lys Asn Leu Leu Tyr Leu Met Pro Ala Lys Thr Val Lys Pro Gly
        515                 520                 525
Arg Asp Glu Pro Glu Val Leu Pro Val Leu Ser Glu Ser
530                 535                 540
```